US011008575B2

(12) United States Patent
Richardson et al.

(10) Patent No.: US 11,008,575 B2
(45) Date of Patent: May 18, 2021

(54) DNA APTAMERS AGAINST CANCER AND USES THEREOF IN DELIVERY OF THERAPY AND DIAGNOSIS OF CANCER

(71) Applicant: The University of North Carolina at Charlotte, Charlotte, NC (US)

(72) Inventors: Christine Richardson, Charlotte, NC (US); Gregory Benedetto, Charlotte, NC (US)

(73) Assignee: The University of North Carolina at Charlotte, Charlotte, NC (US)

( * ) Notice: Subject to any disclaimer, the term of this patent is extended or adjusted under 35 U.S.C. 154(b) by 94 days.

(21) Appl. No.: 15/437,244

(22) Filed: Feb. 20, 2017

(65) Prior Publication Data

US 2017/0233739 A1 Aug. 17, 2017

Related U.S. Application Data

(63) Continuation-in-part of application No. 15/210,419, filed on Jul. 14, 2016, now abandoned.

(60) Provisional application No. 62/197,725, filed on Jul. 28, 2015.

(51) Int. Cl.
| | |
|---|---|
| *A61K 48/00* | (2006.01) |
| *C07H 21/04* | (2006.01) |
| *C12N 15/115* | (2010.01) |
| *G01N 33/574* | (2006.01) |
| *G01N 33/53* | (2006.01) |
| *A61K 9/00* | (2006.01) |
| *A61K 49/00* | (2006.01) |
| *A61K 47/54* | (2017.01) |
| *A61K 47/69* | (2017.01) |

(52) U.S. Cl.
CPC .......... *C12N 15/115* (2013.01); *A61K 9/0019* (2013.01); *A61K 47/549* (2017.08); *A61K 47/6937* (2017.08); *A61K 49/0032* (2013.01); *A61K 49/0054* (2013.01); *A61K 49/0093* (2013.01); *G01N 33/5308* (2013.01); *G01N 33/57449* (2013.01); *C12N 2310/16* (2013.01); *C12N 2310/351* (2013.01); *C12N 2310/3517* (2013.01)

(58) Field of Classification Search
CPC ... C12N 15/113; C12N 2310/16; A61K 45/06
See application file for complete search history.

(56) References Cited

U.S. PATENT DOCUMENTS

| 8,138,319 | B2 * | 3/2012 | Oksenberg | ........... C12N 5/0612 436/501 |
|---|---|---|---|---|
| 9,644,202 | B2 * | 5/2017 | Berezovski | ........... C12N 15/111 |
| 10,221,420 | B2 * | 3/2019 | Duan | ................... G01N 33/574 |
| 2016/0061840 | A1 | 3/2016 | Lee et al. | |

FOREIGN PATENT DOCUMENTS

RU 2501862 C1 * 12/2013

OTHER PUBLICATIONS

Benedetto et al., Nucleic Acid Ther, Jun. 2015, 25(3), 162-172.*
Mallikaratchy et al., "A multivalent DNA aptamer specific for the B-cell receptor on human lymphoma and leukemia," Nucleic Acids Res., 39(6):2458-2469. (Mar. 2011). Epub (Oct. 2010).
Masiakos et al., "Human ovarian cancer, cell lines, and primary ascites cells express the human Mullerian inhibiting substance (MIS) type II receptor, bind, and are responsive to MIS," Clin. Cancer Res., 5(11):3488-3499. (Nov. 1999).
Moore et al., "A novel multiple marker bioassay utilizing HE4 and CA125 for the prediction of ovarian cancer in patients with pelvic mass," Gynecol. Oncol., 112(1):40-46. (Jan. 2009). Epub (Oct. 2008).
Ng et al., "Anti-VEGF aptamer (pegaptanib) therapy for ocular vascular diseases," Ann N Y Acad. Sci., 1082:151-171. (Oct. 2006).
Ng et al., "Pegaptanib, a targeted anti-VEGF aptamer for ocular vascular disease," Nat Rev. Drug Discov., 5 (2):123-132. (Feb. 2006).
Rockman et al., "Control of myocardial contractile function by the level of beta-adrenergic receptor kinase 1 in gene-targeted mice," J. Biol. Chem., 273(29):20556-20567. (Jul. 1998).
Saad et al., "Microenvironment and pathogenesis of epithelial ovarian cancer," Horm. Cancer, 1(6):277-290. (Dec. 2010).
Sayari et al., "MUC1 aptamer conjugated to chitosan nanoparticles, an efficient targeted carrier designed for anticancer SN38 delivery," Int J Pharm 473(1-2):304-15. (Oct. 2014). Epub (Jun. 2014).
Shangguan et al., "Indentification of liver cancer-specific aptamers using whole live cells," Anal. Chem., 80 (3):721-728. (Feb. 2008). Epub (Jan. 2008).
Shiao et al., "Aptamer-functionalized gold nanoparticles as photoresponsive nanoplatform for co-drug delivery," ACS Appl Mater Interfaces, 6(24):1832-41. (Dec. 2014). Epub (Jun. 2014).
Shum et al., "Nucleic acid aptamers as potential therapeutic and diagnostic agents for lymphoma," J. Cancer Ther., 4 (4):872-890. (Jun. 2013).
Sorace et al., "A data review and re-assessment of ovarian cancer serum proteomic profiling," BMC Bioinformatics, 4:24, (Jun. 2003).
Soundararajan et al., "The nucleolin targeting aptamers AS1411 destablizes Bcl-2 messenger RNA in human breast cancer cells," Cancer Res., 68(7):2358-2365. (Apr. 2008).
Taghdisi et al., "Targeted delivery of epirubicin to cancer cells by PEGylatd A10 aptamer," J Drug Target., 21 (8):739-44. (Sep. 2013). Epub (Jul. 2013).
Tang et al., "Selection of aptamers for molecular recognition and characterization of cancer cells," Anal. Chem., 79 (13):4900-4907. (Jul. 2007). Epub (May 2007).

(Continued)

*Primary Examiner* — Amy H Bowman
(74) *Attorney, Agent, or Firm* — McDonnell Boehnen Hulbert & Berghoff LLP

(57) ABSTRACT

Disclosed herein are unique single stranded DNA oligonucleotide products identified as binding with high affinity and specificity to ovarian tumor cells that may be used in the delivery of therapy to and diagnosis of ovarian cancer.

22 Claims, 20 Drawing Sheets

Specification includes a Sequence Listing.

(56) References Cited

OTHER PUBLICATIONS

Tolentino et al., "Drugs in Phase II clinical trials for the treatment of age-related macular degeneration," Expert Opin. Investig. Drugs., 24(2):183-199. (Feb. 2015). Epub (Sep. 2014).
Tsao et al., "Characterization of human ovarian surface epithelial cells immortalized by human papilloma viral oncogenes (HPV-E6E7 ORFs)," Exp. Cell Res., 218(2):499-507. (Jun. 1995).
Van Simaeys et al., "Study of the molecule recognition of aptamers selected through ovarian cancer cell-SELEX," PLoS One, 5(11):e13770. (Nov. 2010).
Yip et al., "Comprehensive serum profiling for the discovery of epithelial ovarian cancer biomarkers," PLoS One, 6 (12):e29533. (2011).
Yu et al., "Novel aptamer-nanoparticle bioconjugats enhances delivery of anticancer drug to MUC1-positive cancer cells in vitro," PLoS One 6(9):e24077. (2011). Epub (Sep. 2011).
Zhan et al., "Recent progress on SELEX and its applications," Bind Du Xue Bao, 29(5):573-77. (Sep. 2013) (English Abstract).
Zhang et al., "A cell-based single-stranded DNA aptamer specifically targets gastric cancer," Int. J. Biochem. Cell Biol., 46:1-8. (Jan. 2014).
Zhang et al., "A novel aptamer developed for breast cancer cell internalization," Chem Med Chem, 7(1):79-84. (Jan. 2012). Epub (Dec. 2011).
Zhang et al., "Biocatalytic release of an anticancer drug from nucleic-acids-capped meoporous SiO2 using DNA or molecular biomarkers as triggering stimuli," ACS Nano, 7(10):8455-68. (Oct. 2013). Epub (Sep. 2013).
Zhang et al., "Three biomarkers identified from serum proteomic analysis for the detection of early stage ovarian cancer," Cancer Res. 64(16):5882-5890. (Aug. 2004).
Zhou et al., "Aptamer-nanopartile bioconjugates enhance intracellular delivery of vinorelbine to breast cancer cells," J Drug Target, 22(1):57-66. (Jan. 2014). Epub (Oct. 2013).
Zhou et al.,"Aptamer-based biosensors for biomedical diagnostics" Analyst, 139(11):2627-2640. (Jun. 2014).
Zhu et al., "Progress in aptamer-mediated drug delivery vehicles for cancer targeting and its implications in addressing chemotherapeutic challenges," Theranostics, 4(9):931-944. (Jul. 2014).
Zhu et al., "Self-assembled aptamer-based drug carriers for bispecific cytotoxicity to cancer cells," Chem Asian J., 7 (7)1630-6. (Jun. 2012). Epub (Apr. 2012).
Abouzeid et al., "Polyethyene glycol-phosphatidylethanolamine (PEG-PE)/vitamin E micelles for co-delivery of paclitaxel and curcumin to overcome multi-drug resistance in ovarian cancer," Int. J. Pharm., 464(1-2):178-184. (Apr. 2014). Epub (Jan. 2014).
Aravind et al., "AS1411 aptamer tagged PLGA-lechithin-PEG nanoparticles for tumor cell targeting and drug delivery," Biotechnol Bioeng, 109(11):2920-31. (Nov. 2012). Epub (Jun. 2012).
Bates et al., "Antiproliferative activity of G-rich oligonucleotides correlates with protein binding," J. Biol. Chem, 274 (37):26369-26377. (Sep. 1999).
Beaufort et al., "Ovarian cancer cell line panel (OCCP): clinical importance of in vitro morphological subtypes," PLoS One 9(9):e103988. (Sep. 2014).
Bell et al., "Oligonucleotide NX1838 inhibits VEGF165-mediated cellular responses in vitro," In Vitro Cell Dev. Biol. Anim., 35(9):533-542. (Oct. 1999).
Bicaku et al., "In vitro analysis of ovarian cancer response to cisplatin, carboplatin, and paclitaxel identities common pathways that are also associated with overall patient survival," Br. J. Cancer., 106(12):1967-1975. (Jun. 2012). Epub (May 2012).
Biesecker et al., "Derivation of RNA aptamer inhibitors of human complement C5," Immunopharmacology, 42 (1-3):219-230. (May 1999).
Brody et al., "Aptamers as therapeutic and diagnostic agents," J. Biotechnol., 74(1):5-13. (Mar. 2000).
Buick et al., Comparative properties of five human ovarian adenocarcinoma cell lines, Cancer Res, 45(8):3668-76. (Aug. 1985).

Cerchia et al., "Targeting Axl with an high-affinity inhibitory aptamer," Mol. Ther., 20(12):2291-2303. (Dec. 2012). Epub (Aug. 2012).
Choi et al., "Conditional survival in ovarian cancer: results for the SEER dataset 1988-2001," Gynecol. Oncol., 109 (2)203-209. (May 2008). Epub (Mar. 2008).
Cohen et al., "In 2014, can we do better than CA125 in the early detection of ovarian cancer?," World J. Biol. Chem., 5(3):286-300. (Aug. 2014).
Conic et al., "Ovarian epithelial cancer stem cells," ScientificWorldJournal, 11:1243-1269. (Jun. 2011).
Crum et al., "Lessons from BRCA: the tubal fimbria emerges as an origin for pelvic serous cancer," Clin. Med. Res. 5 (1):35-44. (Mar. 2007).
Cunningham et al., "A phase II randomized double-masked trial of pegaptanib, an anti-vascular endothelial growth factor aptamer, for diabetic macular edema," Ophthalmology, 112(10):1747-1757. (Oct. 2005).
Daniels et al., "A tenascin-C aptamer identified by tumor cell SELEX: systematic evolution of ligands by exponential enrichment," Proc Natl Acad Sci USA 100(26):15416-21. (Dec. 2003).
Dhar et al. "Targeted delivery of a cisplatin prodrug for sager and more effective prostate cancer therapy in vivo," Proc Natl Acad Sci USA, 108(5):1850-5. (Feb. 2011). Epub (Jan. 2011).
Dhar et al. "Targeted delivery of cisplatin to prostate cancer cells by aptamer functionalized Pt9IV) prodrug-PLGA-PEG nanoparticles," Proc Natl Acad Sci USA, 105(45):17356-61. (Nov. 2008).
Dubeau, "The cell of origin of ovarian epithelial tumors," Lancet Oncol., 9(12):1191-1197. (Dec. 2008).
Furlong et al., "Evidence for the colonic origin of ovarian cancer cell line SW626," J. Natl. Cancer Inst., 91 (15):1327-1328. (Aug. 1999).
Girvan et al., "AGRO100 inhibits activation of nuclear factor-kappB (NF-kappaB) by forming a complex with NF-kappaB essential modulator (NEMO) and nucleolin," Mol. Cancer Ther., 5(7)1790-1799. (Jul. 2006).
Guo et al., "Aptamer-functionalized PEG-PLGA nanoparticles for enhanced anti-glioma drug delivery," Biomaterials 32 (31):8010-20. (Nov. 2011). Epub (Jul. 2011).
He et al., "One-pot synthesis of sustained-released doxorubicin silica nanoparticles for aptamer targeted delivery to tumor cells," Nanoscale, 3(7):2936-42. (Jul. 2011). Epub (May 2011).
Hellstrom et al., "SMRP and HE4 as biomarkers for ovarian carcinoma when used alone and in combination with CA125 and/or each other," Adv. Exp. Med. Biol., 622:15-21. (2008).
Hennessy et al., "Ovarian cancer," Lancet, 374(9698):1371-1382, (Oct. 2009). Epub (Sep. 2009).
Herfs et al., "A discrete population of squamocolumnar junction cells implicated in pathogenesis of cervical cancer," Proc. Natl. Acad. Sci. USA, 109(26):10516-10521, (Jun. 2012). Epub (Jun. 2012).
SEER Cancer Stat Facts: Ovarian Cancer, National Cancer Institute, based on Nov. 2017 SEER data submission, posted to the SEER web site, Apr. 2018 (retrieved from the internet seer.cancer.gov/statfacts/html/ovary.html) (11 pages).
Ireson et al., "Discovery and development of anticancer aptamers," Mol. Cancer Ther., 5(12):2957-2962. (Dec. 2006).
Iwamura et al., "Establishment and characterization of a human pancreatic cancer cell line (Suit-2) producing carcinoembryonic antigen and carbohydrate antigen 19-9," Jpn J Cancer Res 78:54-62 (1987).
Jacobs et al., "A risk of malignancy index incorporating CA125, ultrasound and menopausal status for the accurate preoperative diagnosis of ovarian cancer," Br. J. Obstet. Gynaecol., 97(10):922-929. (Oct. 1990).
Jalalian et al., "Epirubicin loaded super paramagnetic iron oxide nanoparticle-aptamer bioconjugate for combined colon cancer therapy and imaging in vivo," Eur. J. Pharm. Sci., 50(2):191-197. (Oct. 2013). Epub (Jul. 2013).
Kim et al., "Prostate cancer cell death produced by the co-delivery of Bcl-xL shRNA and doxorubicin using an aptamer-conjugated polyplex," Biomaterials 31(16):4592-9. (Jun. 2010). Epub (Mar. 2010).

(56) References Cited

OTHER PUBLICATIONS

Kolishetti et al., Engineering of self-assembled nanoparticle platform for precisely controlled drug therapy, Proc Natl Acad Sci USA, 107(42):17939-44. (Oct. 2010).
Kroep, "Advances in epithelial ovarian cancer therapy," Curr. Pharm. Des., 18(25):3735-3740 (2012).
Kruspe et al., "Chlorin e6 conjugated interleukin-6 receptor aptamers selectively kill target cells upon irradiation," Mol. Ther. Nucleic Acids, 3:e143. (Jan. 2014).
Lee et al., "Targeted chemoimmunotherapy using drug-loaded aptamer-dendrimer bioconjugates," J. Control Release, 155(3):435-41. (Nov. 2011). Epub (May 2011).
Li et al., "A vitamin-responsive mesoporous nanocarrier with DNA aptamer-mediated cell targeting," Chem Commun (Camb), 49(52):5823-5. (Jul. 2013). Epub (Apr. 2013).
Li et al., "Epithelial cell adhesion molecule aptamer functionalized PLGA-lecithin-curcumin-PEG nanoparicles for targeted drug delivery to human colorectal adenocarcinoma cells," Int J Nanomedicine, 9:1083-96. (Feb. 2014).
Li et al., "Nucleolin-targeting liposomes guided by aptamer AS1411 for the delivery of siRNA for the treatment of malignant melanomas", Biomaterials, 35(12):3840-50. (Apr. 2014). Epub (Jan. 2014).
Liu et al., "Novel HER2 aptamer selectively delivers cytotoxic drug to HER2-positive breast cancer cells in vitro," J. Transl Med, 10:148. (Jul. 2012).
Lyu et al., "Generating cell targeting aptamers for nanotheranostics using Cell-SELEX," Theranosistics, 6 (9):1440-1452. (Jun. 2016).
Lin et al., "A novel aptamer functionalized CuInS2 quantum dots probe for daunorubicin sensing and near infrared imaging of prostate cancer cells," Anal Chim Acta, 818:54-60 (Mar. 2014). Epub (Feb. 2014).

\* cited by examiner

Portion of figure adapted from Tan et al. 2016 Theranoistics 6(9):1440-1452.

Figure 5A
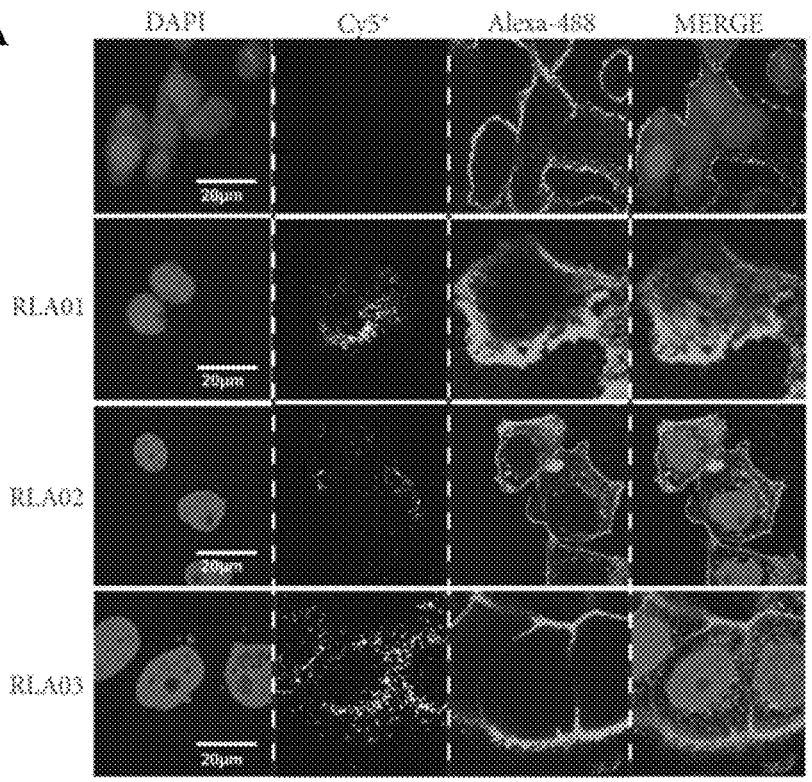
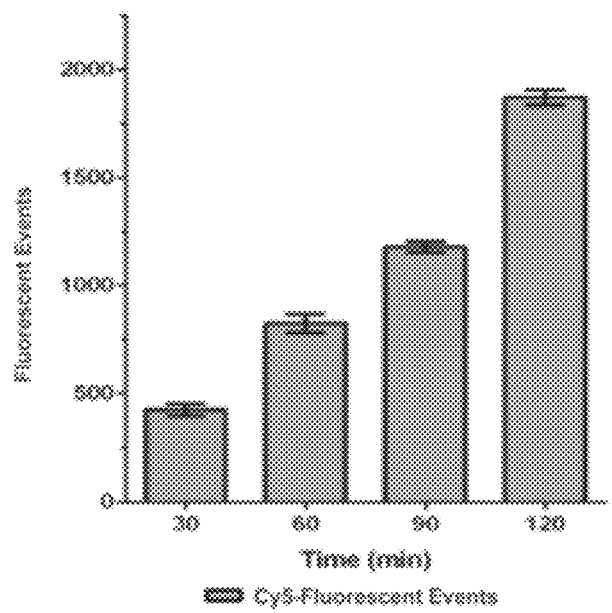
Figure 5B
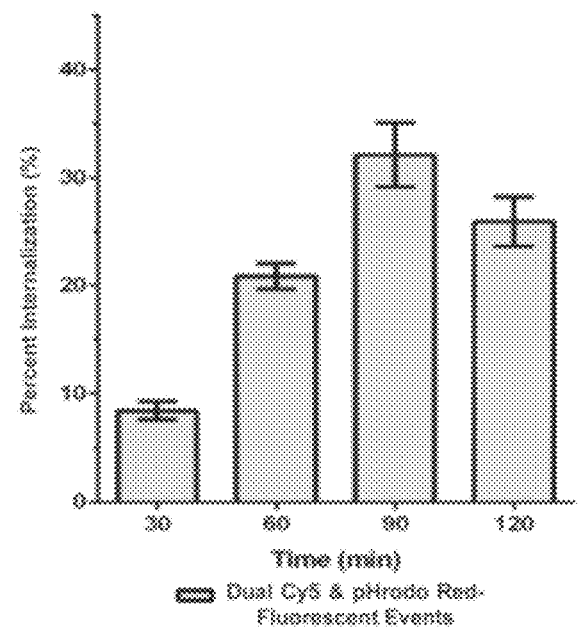
Figure 5C (A-F = SEQ ID NO: 1)

RLA01

| | ΔG (kcal*mole-1) |
|---|---|
| A | -2.4 |
| B | -2.34 |
| C | -2.24 |
| D | -2.08 |
| E | -1.47 |
| F | -1.43 |

(A-G = SEQ ID NO: 2)

| RLA02 | ΔG (kcal*mole-1) |
|---|---|
| A | -4.9 |
| B | -3.93 |
| C | -3.72 |
| D | -3.65 |
| E | -3 |
| F | -2.99 |
| G | -2.8 |

(A-G = SEQ ID NO: 3)

RLA03

| | ΔG (kcal*mole-1) |
|---|---|
| A | -4.21 |
| B | -4.02 |
| C | -3.39 |
| D | -2.91 |
| E | -2.82 |
| F | -2.22 |
| G | -2.15 |

RLA04

ΔG (kcal^mole-1)

A  -1.30
B  -1.16
C  -0.89

(A-C = SEQ ID NO: 4)

RLA05

| ΔG (kcal^mole-1) |
|---|
| A -3.68 |

(SEQ ID NO: 5)

(A-F = SEQ ID NO: 6)

RLA06

| ΔG (kcal^mole-1) |
|---|
| A -2.46 |
| B -2.46 |
| C -3.01 |
| D -3.12 |
| E -3.32 |
| F -3.4 |

(A-F = SEQ ID NO: 7)

RLA07

ΔG (kcal^mole-1)

A  -3.55
B  -3.63
C  -3.74
D  -3.97
E  -4.03
F  -4.21

Figure 15A 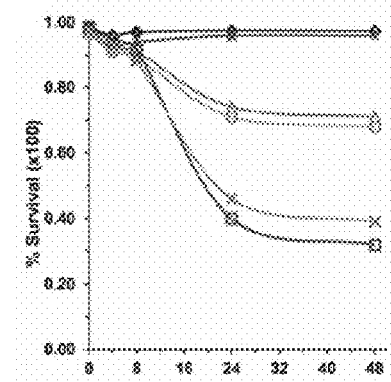 Figure 15B 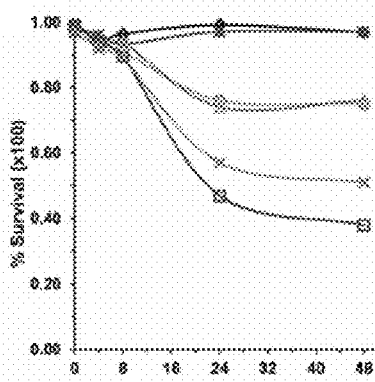 Figure 15C 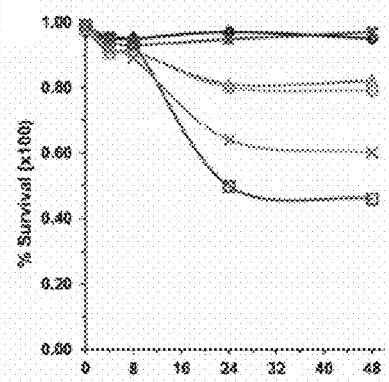
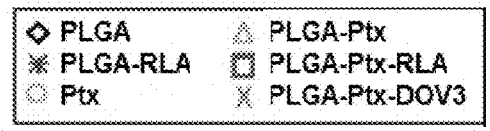
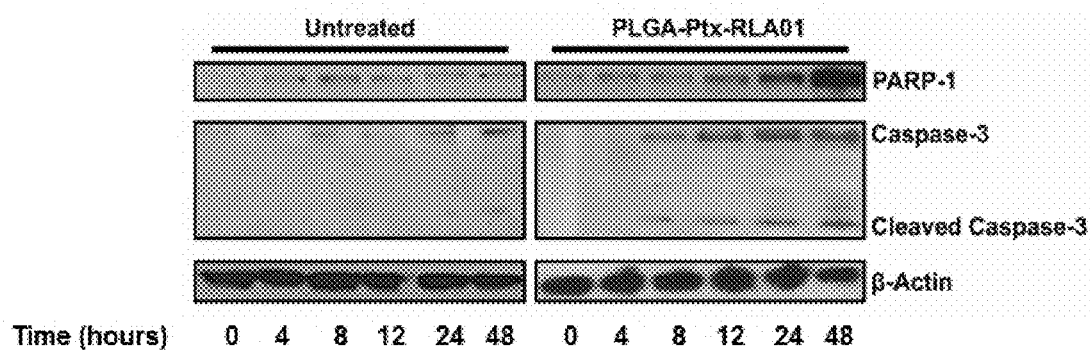
Figure 15D

DNA APTAMERS AGAINST CANCER AND USES THEREOF IN DELIVERY OF THERAPY AND DIAGNOSIS OF CANCER

CROSS-REFERENCE TO RELATED APPLICATIONS

This application is a continuation-in-part of U.S. patent application Ser. No. 15/210,419, filed on Jul. 14, 2016, which claims priority to U.S. Provisional Patent Application No. 62/197,725, filed Jul. 28, 2015, the disclosure of each of which is hereby incorporated by cross-reference in its entirety.

BACKGROUND

Epithelial ovarian cancer (EOC) is one of the most common and highly malignant diseases affecting women. In 2014, the most recent year that statistics have been released, almost 22,000 new cases of EOC were diagnosed with over 14,000 EOC related deaths in the Unites States alone (Howlander et al., 2016, SEER Cancer Statistics Review, National Cancer Institute). Since the majority of EOC are diagnosed at stage II or later, there are fewer treatment options for patients and poor long-term prognosis with a 5-year mean survival rate of 44%. Moreover, the relative survival rate decreases to 27% when EOC is diagnosed at stage III which constitutes almost 62% of all new cases each year (Choi et al., (2008) Gynecol. Oncol. 109:203-209). Current treatment regimens include surgical resection of malignant tissue followed by adjuvant platinum-taxane combination therapy giving a high rate of initial response, but 60% to 75% of patients demonstrate local recurrence (Kroep (2012) Curr. Pharm. Des. 18:3735-3740; Bicaku et al., (2012) Br. J Cancer 106:1967-1975).

There remains limited understanding of the pathogenesis of ovarian tumors due to the heterogeneous nature of the disease. Subtypes include serous, endometrioid, mucinous, clear cell, transitional cell, squamous cell, mixed epithelial, and undifferentiated (Conic et al. (2011) Scientific World Journal 11:1243-1269). Further, the origin of tumors is difficult to understand since the physical development of cyst-like structures within the ovary is uncharacteristic of normal epithelial ovarian tissue (Dubeau, (2008) Lancet Oncol. 9:1191-1197), and at least a portion of serous ovarian tumors likely originate within the fallopian tube (Dubeau, (2008) Lancet Oncol. 9:1191-1197).

Genome wide studies on the proteome and transcriptome abnormalities of EOC generated a large number of potential tumor biomarkers, including CA-125 and WFDC2 (HE4) proteins (Cohen et al., (2014) World J. Biol. Chem. 5:286-300; Hellstrom et al., (2008) Adv. Exp. Med. Biol. 622:15-21; Sorace et al., (2003) BMC Bioinformatics 4:24). A widely accepted Risk of Malignancy Index (RMI) is used to differentiate between a malignant and benign abdominal mass (Jacobs et al., (1990) Br. J. Obstet. Gynaecol. 97:922-929). The criteria used include a woman's age, ultrasound score, menopausal status, a clinical impression score, and serum CA-125 count. The Risk of Malignancy Algorithm (RMA) improved upon RMI by including an additional biomarker HE4 (Moore et al., (2009) Gynecol. Oncol. 112:40-46), and the OVA1 blood tests includes a panel of five biomarkers which include CA125, HE4, transferrin, prealbumin, and β2 microglobulin (Zhang et al., (2004), Cancer Res. 64:5882-5890); however, comprehensive serum studies evaluating the effectiveness of RMI, ROMA, and OVA1 blood tests have given conflicting results and still fail to promote early detection of EOC (Cohen et al., (2014) World J. Biol. Chem. 5:286-300; Yip et al., (2011) PLoS One 6:e29533).

Alternative approaches to generate more sensitive diagnostic tools to aid in early detection of EOC include recognition of novel or existing tumor markers and membrane structures in their native state on the cell surface of EOC cells. Aptamers are single-stranded (ss) DNA/RNA oligonucleotides that fold into complex secondary and tertiary structures that enable them to bind with antibody-like properties to multiple targets. Aptamers have been used as probes for diagnostic identification of tumors in vivo, as single molecule antagonists, and as directed therapy agents when conjugated to chemotherapeutics or small molecule vehicles both in vitro and in vivo (Kruspe et al., (2014) Mol. Ther. Nucleic Acids 3:e143; Zhu et al., (2014) Theranostics 4:931-944; Brody et al., (2000) J. Biotechnol. 74:5-13; Zhou et al., (2014) Analyst 139:2627-2640; Shum et al., (2013) J. Cancer Ther. 4:872-890; Jalalian et al., (2013) Eur. J. Pharm. Sci. 50:191-197; Cunningham et al., (2005) Ophthalmology 112:1747-1757).

The potential clinical significance of aptamers has grown significantly (Research 2013) with reports of several clinical trials including Macugen (pegaptanib) to inhibit VEGF-165 mediated ocular neovascularization in age related macular degeneration (AMD) (Ng and Adamis, (2006) Ann NY Acad. Sci. 1082:151-171; Ng et al., (2006) Nat. Rev. Drug Discov. 5:123-132), and Fovista, the anti-PDGF-β aptamer to treat wet AMD (Tolentino et al., (2014) Expert Opin. Investig. Drugs 24:183-199). Additional antagonistic aptamers disrupt complement component 5 (ARC1905) (Biesecker et al., (1999) Immunopharmacology 42:219-230), bind tumor specific antigens such as B-cell receptors on human lymphoma and leukemia (Mallikaratchy et al., (2011) Nucleic Acids Res. 39:2458-2469), as well as a pro-apoptotic AS1411 aptamer that targets nucleolin and inhibits nuclear factor-κB and Bcl-2 (Soundararajan et al., (2008) Cancer Res. 68:2358-2365; Girvan et al., (2006) Mol. Cancer Ther. 5:1790-1799). Since biomarkers on the surface of specific tumor subtypes is not always known, protocols such as whole Cell-SELEX (Systematic Evolution of Ligands by Exponential enrichment) can be used to screen for unique aptamers based on their ability to bind to the target tumor cells. Notably, aptamers have been identified by whole Cell-SELEX that can bind to the HGC-27 gastric cancer cell line and to paraffin-embedded primary gastric tumor sections (Zhang et al., (2014) Int. J. Biochem. Cell Biol. 46:1-8).

Since ovarian cancer is often diagnosed in late stages with few treatment options and poor long-term prognosis, there is a need for new clinical tools for early detection and treatment of ovarian malignancies, which will significantly help reduce mortality and improve current long-term survival rates. Additionally, development of targeted therapies to selectively deliver anti-cancer agents to tumor cells without damaging neighboring unaffected cells would improve response rates and outcome. Described herein are novel DNA oligonucleotides that bind to malignant ovarian tumor cells and internalize with high affinity and specificity.

BRIEF SUMMARY OF THE INVENTION

The present disclosure is based in part on the discovery of unique aptamers that have clinical relevance for detection and diagnosis of ovarian cancer or as targeting agents when conjugated to the surface of nanoparticles loaded with chemotherapeutics to promote drug delivery specifically to ovarian tumor cells.

One aspect of the present invention provides an aptamer comprising a nucleotide sequence that has at least 80% sequence identity to the nucleotide sequence CTCCTCTGACTGTAACCACG-$N_x$-GCAT-AGGTAGTCCAGAAGCCA (SEQ ID NO: 9); wherein N is a nucleotide selected from the group consisting of G, C, A, or T; x is 19 or 20 nucleotides; and the aptamer selectively binds to an ovarian tumor cell. In certain embodiments, the aptamer comprises a nucleotide sequence that has at least 90% sequence identity to the nucleotide sequences set forth in any of SEQ ID NOS: 1-7. In other embodiments, the aptamer comprises the nucleotide sequence set forth in any of SEQ ID NOS: 1-7.

In another embodiment, the ovarian tumor cell is an epithelial ovarian cancer (EOC) cell. In yet another embodiment, the epithelial ovarian cancer (EOC) cell is a Caov-3 adenocarcinoma cell. In yet another embodiment, the aptamer selectively binds to an ovarian tumor cell and not a non-malignant neighboring cell. In certain embodiments, the aptamer is capable of being internalized into cancer cells, and in particularly an epithelial ovarian cancer (EOC).

In another embodiment, the aptamer is conjugated to a diagnostic agent. In another embodiment, the diagnostic agent is selected from a radioactive substance, a dye, a contrast agent, a fluorophore molecule, or a bioluminescent molecule. In another embodiment, the diagnostic agent is a cyanine dye.

In yet another embodiment, the aptamer is conjugated to a nanoparticle. In certain embodiments, the aptamer is conjugated to a therapeutic agent. In other embodiments, the therapeutic agent is a chemotherapeutic agent. In yet other embodiments, the chemotherapeutic agent is paclitaxel or carboplatin.

Another aspect of the present disclosure provides a pharmaceutical composition comprising an aptamer comprising a nucleotide sequence that has at least 80% sequence identity to the nucleotide sequence CTCCTCTGACTGTAAC-CACG-$N_x$-GCATAGGTAGTCCAGAAGCCA (SEQ ID NO: 9); wherein N is a nucleotide selected from the group consisting of G, C, A, or T; x is 19 or 20 nucleotides; and the aptamer selectively binds to an ovarian tumor cell, and a pharmaceutically acceptable carrier.

Another aspect of the present disclosure provides a method of treating ovarian cancer in a subject in need thereof comprising administering to a subject a therapeutically effective amount of an aptamer comprising a nucleotide sequence that has at least 80% sequence identity to the nucleotide sequence CTCCTCTGACTGTAACCACG-$N_x$-GCATAGGTAGTCCAGAAGCCA (SEQ ID NO: 9); wherein, N is a nucleotide selected from the group consisting of G, C, A, or T, x is 19 or 20 nucleotides; the aptamer is conjugated to a therapeutic agent, wherein the aptamer localizes and binds to an ovarian tumor cell, resulting in internalization of the aptamer.

In certain embodiments, the aptamer is administered to the subject intravenously. In other embodiments, the therapeutic agent is a chemotherapeutic agent. In yet other embodiments, the chemotherapeutic agent is paclitaxel or carboplatin.

Yet another aspect of the present disclosure provides a method of diagnosing ovarian cancer in a subject in need thereof comprising: contacting an ovarian cell with an aptamer comprising a nucleotide sequence that has at least 80% sequence identity to the nucleotide sequence CTCCTCTGACTGTAACCACG-$N_x$-GCAT-AGGTAGTCCAGAAGCCA (SEQ ID NO: 9); wherein N is a nucleotide selected from the group consisting of G, C, A, or T; x is 19 or 20 nucleotides; the aptamer selectively binds to an ovarian tumor cell; and the aptamer is conjugated to a diagnostic agent; and detecting a signal generated by the diagnostic agent to indicate the presence of an ovarian tumor cell.

In certain embodiments, the diagnostic agent is a cyanine dye. In some embodiments, the diagnostic agent is detected by flow cytometry and/or confocal imaging.

Yet another aspect of the present disclosure provides for all that is disclosed and illustrated herein.

BRIEF DESCRIPTION OF THE DRAWINGS

The foregoing aspects and other features of the invention are explained in the following description, taken in connection with the accompanying drawings, wherein:

FIG. 3A is a graph of Cy5-RLA01 aptamer conjugates with Caov-3 target cells and non-target SK-OV-3 and SW626 cell lines in increasing nM doses. FIG. 3B is a graph of Cy5-RLA02 aptamer conjugates with Caov3 target cells and non-target SK-OV-3 and SW626 cell lines in increasing nM doses.

FIG. 3C is a graph of Cy5-RLA03 aptamer conjugates with Caov-3 target cells and non-target SK-OV-3 and SW626 cell lines in increasing nM doses. Individual apparent $K_d$ values were calculated by using the equation Y=Bmax*x^h/($K_d$^h+X^h) for the DNA aptamers.

FIG. 4A is histograms showing flow cytometry analysis of Cy5-RLA01, RLA02, and RLA03 incubated with the indicated cell lines for 2 hours. Aptamer doses corresponding to hisotgrams are control (solid line), 400 nM ( --- - --- line), and 800 nM ( - - - line) concentrations. FIG. 4B is histograms showing flow cytometry analysis of Cy5-RLA01 incubated with the indicated cell lines for 4 hours at control, 400 nM, and 800 nM concentrations. FIG. 4C is confocal microscope images of indicated cell lines treated with Cy5-RLA01 imaged at 60× using a nuclear stain (DAPI), a membrane stain (WGA-Alexa Fluor 488), and Cy5-aptamers (Cy5 pseudo). FIG. 4D is histograms showing flow cytometry analysis of Cy5-RLA01 incubated with the indicated cell lines for 2 hours at control, 400 nM, and 800 nM concentrations (top) and a binding kinetics graph of RLA01 when increasing nanomolar (nM) concentrations are incubated with Caov-3 (●), SK-OV-3 (■), and HeLa (▲) (bottom). Data points represent the average fluorescent events observed (n=3, error bars±SD) at indicated nM concentrations and individual apparent $K_d$ values were calculated by using the equation $Y=Bmax*x^h/(K_d^h \pm x^h)$.

FIG. 5A-5D shows internalization of RLA01, RLA02, and RLA03 aptamers into Caov-3 cells occurs through the endocytic pathway. FIG. 5A is confocal microscope images of Caov-3 cells treated with Cy5 conjugated RLA01, RLA02, or RLA03 aptamers. Untreated (−) and Cy5-aptamer RLA01, RLA02, and RLA03 conjugate treated cells were imaged at 60× using a nuclear stain (DAPI), a membrane stain (WGA-Alexa Fluor 488), and Cy5-aptamers (Cy5 pseudo). FIG. 5B is a bar graph showing Cy5-RLA01 (500 nM) fluorescent events by flow cytometry observed over 2 hr time course. FIG. 5C is a bar graph showing the percentage of cells showing positive endocytic internalization of Cy5-RLA01 (500 nM) confirmed using pHrodo Red Transferrin Conjugate. FIG. 5D is confocal microscope images of Caov-3 cells that were treated with 5 μM Cy5 conjugated RLA01, RLA02, or RLA03 aptamers. Cells were imaged at 60× using a nuclear stain (DAPI), an endosomal specific marker (pHrodo Red pseudo), and Cy5-aptamers (Cy5 pseudo).

FIG. 6A is confocal microscope images showing 9 image z-stack 0.35 μm slices. FIG. 6B is confocal microscope images showing 9 image z-stack 0.25 μm slices.

FIG. 15A-15D shows graphs of MTT cell proliferation assays and Western blot analysis. FIG. 15A is a graph of MTT cell proliferation assays using RLA01, FIG. 15B is a graph of MTT cell proliferation assays using RLA02, and FIG. 15C is a graph of MTT cell proliferation assays using RLA03. Treatment groups shown in FIG. 15A-15C are: diamond=empty PLGA nanoparticles alone, asterisk=empty PLGA nanoparticles coated with aptamer, circle=Paclitaxel alone, triangle=PLGA nanoparticles loaded with paclitaxel, square=PLGA nanoparticles loaded with paclitaxel and coated with aptamer, cross ("X")=PLGA nanoparticles loaded with paclitaxel and coated with another published aptamer, DOV3. FIG. 15D shows the results of Western blot analysis to determine a time dependent increase of both PARP-1 and Caspase-3 following treatment with Paclitaxel loaded PLGA nanoparticles coated with RLA01 compared to untreated cells.

DETAILED DESCRIPTION OF THE INVENTION

Figure 1:
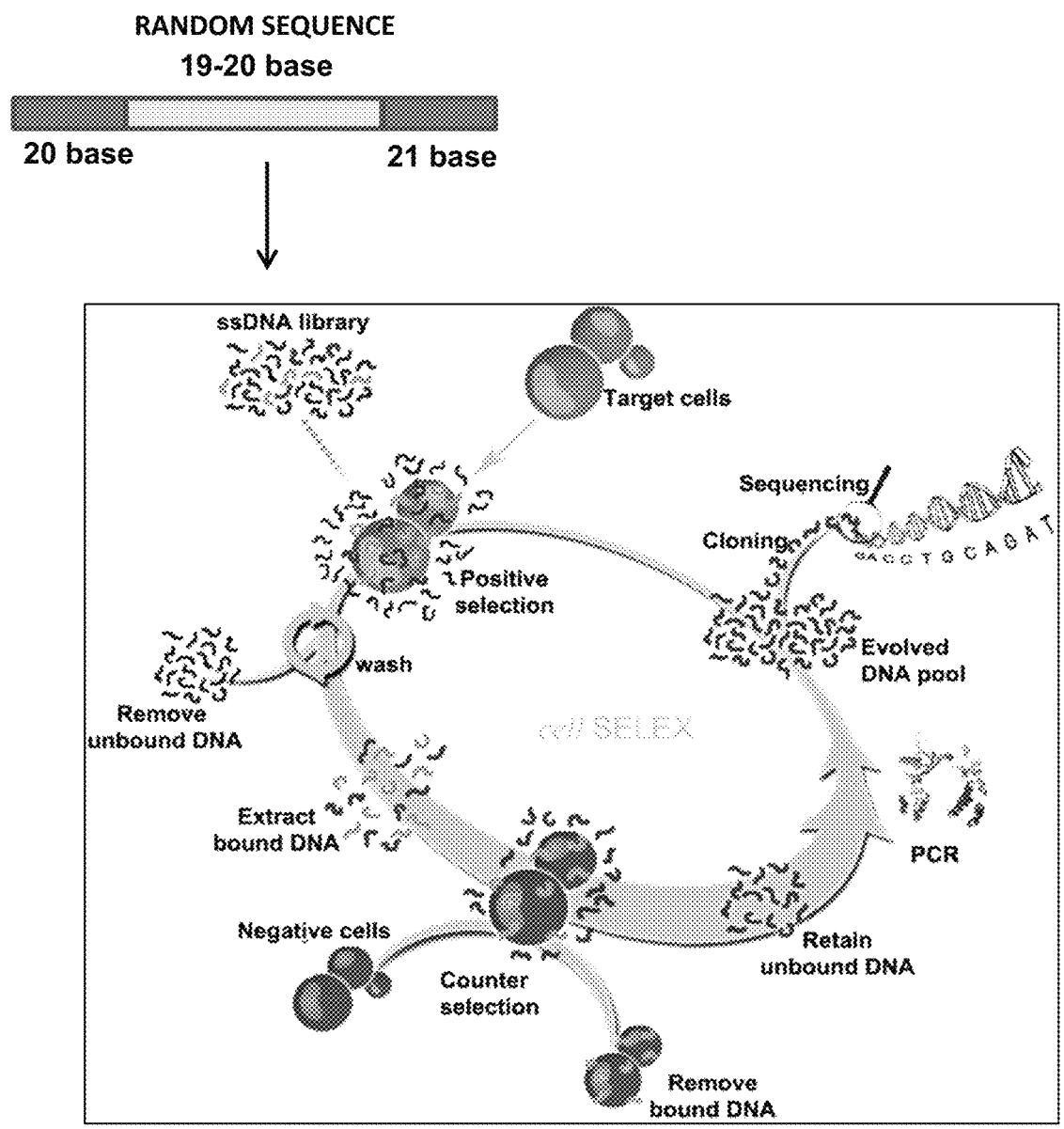
FIG. 1 is a schematic diagram of the Cell-SELEX method used to identify unique aptamers that bind with high affinity and specificity to ovarian tumor cell lines but not non-tumor cells. A portion of this figure was adapted from Tan et al., 2016 *Theranosistics* 6(9): 1440-1452.

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

The present invention relates generally to aptamers that bind with high affinity and specificity to ovarian tumor cell lines but not non-tumor cells.

The term "aptamer" as used herein refers to short single-stranded oligonucleotides or a plurality of said oligonucleotides that bind to target molecules with high affinity, such as a small molecule, protein, nucleic acid, cell, tissue, or organism. Thus, as used herein aptamer denotes both singular and plural sequences of oligonucleotides.

The term "single-stranded" oligonucleotides as used herein refer to those oligonucleotides that contain a single covalently linked series of nucleotide residues.

The terms "oligonucleotides" or "nucleotide sequence" are used interchangeably herein to refer to sequences with conventional bases, sugar residues and internucleotide linkages, but also those which contain modifications of any or all of these three moieties. Oligonucleotides include RNA or DNA sequences of more than one nucleotide in a single chain. "Modified" forms used in candidate pools contain at least one non-native residue.

Particular embodiments of the invention encompass nucleotide aptamers. The terms "nucleotide" as used herein include those moieties which contain not only the natively found purine and pyrimidine bases A, T, C, G and U, but also modified or analogous forms thereof. In certain embodiments, the nucleic aptamer is a DNA aptamer. Such aptamers can identify unique tumor biomarkers, can aid in early detection and diagnosis of neoplastic disorders, and can be functionalized by conjugation to small molecules. Further, such aptamers specifically recognize target cells with an apparent equilibrium dissociation constant ($K_d$) measured in the nanomolar range but show minimal interaction with physiologically similar epithelial tumor cells and non-transformed cell lines. Further, such aptamers internalize into target cells and thus are suited for clinical applications, as a diagnostic tool for detection, visualization including metastasis, or for direct delivery of chemotherapeutics for treatment.

The terms "60mer aptamer sequence" or "60mer" as used herein refers to aptamer sequences that are approximately 60 nucleotides in length and include aptamer sequences that are 60 and 61 nucleotides in length. Examples of 60mer aptamer sequences that are 60 nucleotides in length, include, but are not limited to the nucleotide sequences set forth in SEQ ID NO: 1 (RLA01) and SEQ ID NO: 4 (RLA04). Examples of 60mer aptamer sequences that are 61 nucleotides in length, include, but are not limited to the nucleotide sequences set forth in SEQ ID NO: 2 (RLA02), SEQ ID NO: 3 (RLA03), SEQ ID NO: 5 (RLA05), SEQ ID NO: 6 (RLA06), SEQ ID NO: 7 (RLA07), and the scrambled aptamer (SEQ ID NO: 8).

According to the embodiments described herein, aptamers that specifically bind ovarian cancer cells are generated and selected. Selection of aptamers may be accomplished by any suitable method known in the art, including but not limited to by an in vitro process known as whole Cell-SELEX (Systematic Evolution of Ligands by Exponential enrichment). Briefly, the selection process uses a combinatorial oligonucleotide library in which each oligonucleotide has central region of variable nucleic acids flanked by two regions of fixed sequence. The variable region of each candidate in the library can be totally or partially randomized. The oligonucleotide library is exposed to a target, such as a protein or cell line, under conditions that allow favorable binding between oligonucleotide candidates and the target. Following binding, a selective partitioning step is utilized, in which non-binding or poorly binding oligonucleotides are removed from the mixture, and the oligonucleotide candidates that bound to the target are then removed from the target molecule. These selected oligonucleotides are then enriched using PCR amplification with primers to the fixed regions of the oligonucleotide candidates. This process of binding, selective partitioning, and amplifying the selected candidate oligonucleotides is repeated for several rounds. Finally, the selected sequences are cloned and sequenced.

In some embodiments, a whole Cell-SELEX method used by a number of research laboratories may be used to identify unique aptamers that bind with high affinity and specificity to ovarian tumor cell lines but not non-tumor cells. As described in detail in the Examples below and shown in FIG. 1, this whole Cell-SELEX process uses random single-stranded DNA pools (such as 60 or 61 bases long) to enrich and isolate tumor specific aptamers that bind to tumor specific receptors in their native state on the cell surface through 15 sequential rounds of positive and negative selection, followed by PCR amplification of the enriched pool for use in the subsequent round, with each round resulting in an increasingly concentrated pool. To acquire aptamers with high affinity and specificity, the wash strength is enhanced gradually and flask sizes increased following and including round 10 of positive selection. This analysis may be used to identify aptamers that bind to, and are internalized by, target Caov-3 cell populations but not non-target non-malignant ovarian epithelial HOSE 6-3 cells or multiple other epithelial tumor cell lines.

The aptamers of the present invention form energetically stable secondary and tertiary structures that aid in their binding to target molecules and cells. The structure of the aptamers may be predicted through computerized models know in the art such as, for example, the UNAfold program (Rensselaer Polytechnic Institute). Stability for the aptamers of the present invention may be assessed by determining the Gibbs free energy value ($\Delta G$) for each structure.

One aspect of the present invention provides an aptamer comprising the nucleotide sequence CTCCTCTGACTGTAACCACG-$N_x$-GCAT-AGGTAGTCCAGAAGCCA (SEQ ID NO: 9), wherein N is a nucleotide selected from the group consisting of G, C, A, or T; x is 19 or 20 nucleotides; and the aptamer selectively binds to an ovarian tumor cell. Modifications (i.e., changes in the nucleotide sequence) of the nucleotide sequence set forth in SEQ ID NO: 9 are provided herein. For example, the modifications described herein can be a nucleotide sequence that have at least 60%, 70%, 80%, 85%, 86%, 87%, 88%, 89%, 90%, 91%, 92%, 93%, 94%, 95%, 96%, 97%, 98%, or 99% sequence identity to the nucleotide sequence set forth in SEQ ID NO: 9.

In certain embodiments, the invention includes one or a plurality of unique single stranded DNA oligonucleotide products identified as binding with high affinity and specificity to ovarian tumor cells that may be used in the delivery of therapy to and diagnosis of ovarian cancer. In some embodiments, the aptamers of the present invention have a sequence that may include SEQ ID NO: 1, SEQ ID NO: 2, SEQ ID NO: 3, SEQ ID NO: 4, SEQ ID NO: 5, SEQ ID NO: 6, or SEQ ID NO: 7. In other embodiments, the aptamers of the present invention have at least 60%, 70%, 80%, 85%, 86%, 87%, 88%, 89%, 90%, 91%, 92%, 93%, 94%, 95%, 96%, 97%, 98%, or 99% sequence identity to the nucleotide sequence set forth in any of SEQ ID NO: 1, SEQ ID NO: 2, SEQ ID NO: 3, SEQ ID NO: 4, SEQ ID NO: 5, SEQ ID NO: 6, or SEQ ID NO: 7.

The terms "identity" or "sequence identity" are used herein to refer to the number of identical or similar nucleotide bases on a comparison between a test and reference oligonucleotide or nucleotide sequence. Sequence identity can be determined by sequence alignment of nucleic acid to identify regions of similarity or identity. As described herein, sequence identity is generally determined by alignment to identify identical residues. Matches, mismatches, and gaps can be identified between compared sequences. Alternatively, sequence identity can be determined without taking into account gaps as the number of identical positions/length of the total aligned sequence×100. In one non-limiting embodiment, the term "at least 90% sequence identity to" refers to percent identities from 90 to 100%, relative to the reference nucleotide sequence. Identity at a level of 90% or more is indicative of the fact that, assuming for exemplary purposes a test and reference oligonucleotide length of 100 nucleotides are compared, no more than 10% (i.e., 10 out of 100) of the nucleotides in the test oligonucleotide differ from those of the reference oligonucleotide. Differences are defined as nucleic acid substitutions, insertions, or deletions.

In certain embodiments, the aptamers of the present invention selectively bind to an ovarian tumor cell. In other embodiments, the aptamers of the present invention selectively bind to an epithelial ovarian cancer (EOC) cell. The terms "ovarian tumor cell" and "ovarian cancer cell" are used interchangeably herein to refer to more than 30 different types of ovarian cancer, which are classified by the type of cell from which they originate. The three common ovarian tumor cell types are epithelial cell tumors, also referred to as epithelial ovarian cancer, serous epithelial ovarian cancer, or "EOC", germ cell tumors, and stromal cell tumors. Epithelial ovarian cancer is one of the most common types of ovarian cancer, which develops within the epithelium, the layer of cells that cover the ovary. Some epithelial ovarian cancer may form in the epithelium from a cell that migrated from the fallopian tube to that site to start the tumor. Examples of human epithelial ovarian adenocarcinoma cell lines include, but are not limited to, Caov-3, SK-OV-3, and SW626. In one aspect, the aptamers of the present invention selectively bind to a Caov-3 adenocarcinoma cell.

In certain embodiments, the aptamers of the present invention selectively binds to ovarian tumor cells and not to other non-malignant neighboring cells. Development of targeted therapies to selectively deliver anti-cancer agents to tumor cells, such as ovarian tumor cells, without damaging neighboring unaffected cells would improve response rates and outcome. The terms "non-malignant" and "non-tumor" are used interchangeably herein to refer to cells that are not cancerous. The term "neighboring cells" refers to non-tumor cells of otherwise similar cell type or origin to the ovarian tumor cells. An example of a non-malignant human ovarian epithelial cell line is HOSE 6-3 (HPV immortalized human ovarian surface epithelial cells).

In certain embodiments, the aptamers of the present invention are capable of being internalized into an ovarian tumor cell. In one aspect, the aptamers are capable of being internalized into an epithelial ovarian cancer (EOC) cell.

Another aspect of the present invention are the unique aptamers described herein that have clinical relevance as targeting agents when conjugated to the surface of diagnostic and therapeutic agents for the detection, diagnosis, and treatment of ovarian cancer.

In one embodiment, the aptamers of the present invention may be conjugated to a diagnostic agent. The terms "conjugated" or "conjugate" are used herein to refer to two or more entities that are linked by direct or indirect covalent or non-covalent interaction.

As used herein, the term "diagnostic agent" refers to a substance that is administered to aid in the diagnosis of a disease, including to aid in the diagnosis of ovarian cancer and in particular, epithelial ovarian cancer. Examples of diagnostic agents include, but are not limited to, dyes (e.g., Cy3 or Cy5), fluorophore labels, isotopes (e.g., $^{32}P$, $^{33}P$, $^{35}S$, $^{3}H$, $^{14}C$, $^{125}I$, $^{131}I$) electron-dense reagents (e.g., gold, silver), nano articles enzymes commonly used in an ELISA (e.g., horseradish peroxidase, beta-galactosidase, luciferase, alkaline phosphatase), chemiluminescent compound, colorimetric labels (e.g., colloidal gold), magnetic labels (e.g., Dynabeads™), biotin, digoxigenin, haptens, proteins for which antisera or monoclonal antibodies are available, ligands, hormones, oligonucleotides capable of forming a complex with the corresponding oligonucleotide complement.

Diagnostic agents may be incorporated into nucleic acids by covalent or non-covalent means, such as during transcription. For example, a nucleotide base is conjugated to a detectable moiety, such as a fluorescent dye, e.g., Cy3 or Cy5, and then incorporated into nucleic acid probes during nucleic acid synthesis or amplification. Nucleic acid probes may be labeled when synthesized using Cy3- or Cy5-dCTP conjugates mixed with unlabeled dCTP.

Signals from the diagnostic agent may be detected by various means and will depend on the nature of the diagnostic agent. For example, the diagnostic agent conjugated to the aptamers of the present invention may target to and visualize epithelial ovarian cancer cells in vivo via an imaging method (such as position emission tomography (PET), computer assisted tomography (CAT), single photon emission computerized tomography, x-ray, fluoroscopy, and magnetic resonance imaging (MM). Visualization of a diagnostic agent localized to an organ or location in the body that is susceptible to ovarian cancer, such as on the surface of the ovary, by a diagnostic imaging technique indicates that the subject has or likely has a form of ovarian cancer such as those described above. The diagnostic agent of the present invention may also be detected through in vitro methods by obtaining a tissue sample, such as an ovarian tissue sample, from the subject.

In other embodiments, the aptamers of the present invention may be conjugated to a nanoparticle. The term "nanoparticle" as used herein refers to a biopolymer used as a carrier for drug delivery or diagnostic applications. Examples of biopolymers that may be processed as nanoparticles include, but are not limited to, chemically-modified polysaccharides, and in particular, dextran. Other polymers such as polyesters may be used to form nanoparticles. Polyesters include PLGA, polyanhydride, PCL, poly beta amino esters, or other safe, non-toxic polymers. The term "nanoparticle" also includes, but is not limited to, a nanotube, for example a BCN nanotube, boron nitride nanotube, carbon nanotube, DNA nanotube, gallium nitride nanotube, silicon nanotube, inorganic nanotube, membrane nanotube, or titania nanotubes. Additionally this technology may be used with any non-toxic polymer that can be used in animals.

In other embodiments, the aptamers of the present invention may be conjugated to a therapeutic agent. In certain embodiments, the aptamer-conjugated nanoparticle of the present invention is loaded with a therapeutic agent. As used herein, the term "therapeutic agent" refers to a substance that is capable of producing a curative effect in a disease state. Examples of therapeutic agents include, but are not limited to, alkylating agents, antimetabolites, anti-tumor antibiotics, topoisomerase inhibitors, mitotic inhibitors hormone therapy, targeted therapeutics and immunotherapeutics. In some embodiments the chemotherapeutic agents that may be used as therapeutic agents in accordance with the embodiments of the disclosure include, but are not limited to, 13-cis-Retinoic Acid, 2-Chlorodeoxyadenosine, 5-Azacitidine, 5-Fluorouracil, 6-Mercaptopurine, 6-Thioguanine, actinomycin-D, adriamycin, aldesleukin, alemtuzumab, alitretinoin, all-transretinoic acid, alpha interferon, altretamine, amethopterin, amifostine, anagrelide, anastrozole, arabinosylcytosine, arsenic trioxide, amsacrine, aminocamptothecin, aminoglutethimide, asparaginase, azacytidine, bacillus calmette-guerin (BCG), bendamustine, bevacizumab, bexarotene, bicalutamide, bortezomib, bleomycin, busulfan, calcium leucovorin, citrovorum factor, capecitabine, canertinib, carboplatin, carmustine, cetuximab, chlorambucil, cisplatin, cladribine, cortisone, cyclophosphamide, cytarabine, darbepoetin alfa, dasatinib, daunomycin, decitabine, denileukin diftitox, dexamethasone, dexasone, dexrazoxane, dactinomycin, daunorubicin, decarbazine, docetaxel, doxorubicin, doxifluridine, eniluracil, epirubicin, epoetin alfa, erlotinib, everolimus, exemestane, estramustine, etoposide, filgrastim, fluoxymesterone, fulvestrant, flavopiridol, floxuridine, fludarabine, fluorouracil, flutamide, gefitinib, gemcitabine, gemtuzumab ozogamicin, goserelin, granulocyte-colony stimulating factor, granulocyte macrophage-colony stimulating factor, hexamethylmelamine, hydrocortisone hydroxyurea, ibritumomab, interferon alpha, interleukin-2, interleukin-11, isotretinoin, ixabepilone, idarubicin, imatinib mesylate, ifosfamide, irinotecan, lapatinib, lenalidomide, letrozole, leucovorin, leuprolide, liposomal Ara-C, lomustine, mechlorethamine, megestrol, melphalan, mercaptopurine, mesna, methotrexate, methylprednisolone, mitomycin C, mitotane, mitoxantrone, nelarabine, nilutamide, octreotide, oprelvekin, oxaliplatin, paclitaxel, pamidronate, pemetrexed, panitumumab, PEG Interferon, pegaspargase, pegfilgrastim, PEG-L-asparaginase, pentostatin, plicamycin, prednisolone, prednisone, procarbazine, raloxifene, rituximab, romiplostim, ralitrexed, sapacitabine, sargramostim, satraplatin, sorafenib, sunitinib, semustine, streptozocin, tamoxifen, tegafur, tegafur-uracil, temsirolimus, temozolamide, teniposide, thalidomide, thioguanine, thiotepa, topotecan, toremifene, tositumomab, trastuzumab, tretinoin, trimitrexate, alrubicin, vincristine, vinblastine, vindestine, vinorelbine, vorinostat, or zoledronic acid. In certain embodiments, the therapeutic agent (also referred to as a "chemotherapeutic agent") is paclitaxel or carboplatin.

Additionally, isotopes may be used as therapeutic agents, and include but are not limited to $^{32}P$, $^{33}P$, $^{35}S$, $^{3}H$, $^{14}C$, $^{125}I$, $^{131}I$.

Examples of aptamer-conjugated nanoparticles that have been studied for anti-cancer treatment and detection are described in Table 1.

TABLE 1

Aptamer-Conjugated Nanoparticles in Development for Anti-Cancer Therapy and Detection

| Therapy | Aptamer | Target | Nanoparticle | Findings |
| --- | --- | --- | --- | --- |
| Cisplatin | A10 (RNA) | Prostate specific membrane antigen | PLGA-b-PEG | In vitro (PSMA+ LNCaP cells) internalization/cell viability (Dhar et al. (2008) *Proc Natl Acad Sci USA* 105(45): 17356-61) |
| | A10 (RNA) | Prostate specific membrane antigen | PLGA-b-PEG | In vivo (Sprague Dawley Rats) In vivo toxicity (NUDE BALB/c) xenograph imaging/antitumor effects (Dhar et al. (2011) *Proc Natl Acad Sci USA* 108(5): 1850-5) |

TABLE 1-continued

Aptamer-Conjugated Nanoparticles in Development for Anti-Cancer Therapy and Detection

| Therapy | Aptamer | Target | Nanoparticle | Findings |
|---|---|---|---|---|
| Doxorubicin | KMF2-1a (DNA) | HER2/Erb2 | Drug-Aptamer conjugate | In vitro (MCF-10AT1) internalization/cell viability (Zhang et al. (2012) *Chem Med Chem* 7(1): 79-84) |
| | HB5 (DNA) | Her2/Erb2 | Drug-Aptamer conjugate | In vitro (MDA-MB-231, SK-BR-3) internalization/cell viability (Liu et al. (2012) *J. Transl Med* 10: 148) |
| | sgc8c (DNA) | PTK7 | Silica (SiO$_2$) | |
| | sgc8c (DNA) | PTK7 | Mesoporous Silica (MP-SiO$_2$) | In vitro (Ramos, CCRF-CEM cells) internalization/cell viability |
| | A9 (RNA) | Prostate specific membrane antigen | PAMAM-succinamic acid dendrimer | In vivo (BALB/c) Ex vivo organ imaging (He et al. (2011) *Nanoscale* 3(7): 2936-42) |
| | TDO5-sgc8c-sgd5a | mIGm (B-cell receptor) Protein Kinase 7 Toledo cells (B-cell lymphoma) | Trimeric aptamer linked to Dox (3-D nucleic acid structure) | In vivo (Toledo, Ramos) internalization/cell viability (Li et al. (2013) *Chem Commun (Camb)* 49(52): 5823-5) In vitro (RAW264.7 murine monocytes) immune response (LNCaP, 22RV1) anticancer effects In vivo (BALB/c) antitumor effects (Lee et al. (2011) *J. Control Release* 155(3): 435-41) In vivo (CCRF-CEM, Toledo, Ramos, NB4) internalization/cell viability (Zhu et al. (2012 *Chem Asian J.* 7(7): 1630-6) |
| Epirubicin | MUC-1 (DNA) | Mucin-1 | Iron oxide (FeNO$_3$) | In vitro (CHO-K1, C532 Murine Colon) anticancer effects |
| | A-10 (RNA) | Prostate specific membrane antigen | PEGylated aptamer | In vivo (BALB/c) antitumor effects Mag. Res. Imaging (Jalalian et al. (2013) *Eur J Pharm Sci* 50(2): 191-7) In vitro (PSMA+ LNCaP) internalization/cell viability (Taghdisi et al. (2013) *J Drug Target*) |
| Paclitaxel | MUC-1 (DNA) | Mucin-1 | PLGA | In vitro (MCF-7, HepG2) internalization/cell viability (Yu et al. (2011) *PLoS One* 6(9): e24077 |
| | AS1411 (DNA) | Nucleolin | PLGA-PEG | |
| | AS1411 (DNA) | Nucleolin | PLGA-Lecitin-PEG | In vitro (C6-rat glioma) internalization/cell viability In vivo (Sprague Dawley rats, Wistar rats, NUDE mice) antitumor, tissue distribution, pharmokinetics (Guo et al. (2011) *Biomaterials* 32(31): 8010-20) In vitro (GI-1, L929, MCF-7) internalization/cell viability (Aravind et al. (2012) *Biotechnol Bioeng* 109(11): 2920-31) |
| Camptothecin | ATP specific (DNA) | ATP recruitment promotes release | Mesoporous silica (MP-SiO$_2$) | In vitro (MDA-MB-231, MCF-10a) internalization/cell viability (Zhang et al. (2013) *ACS Nano* 7(10): 8455-68) |

TABLE 1-continued

Aptamer-Conjugated Nanoparticles in Development for Anti-Cancer Therapy and Detection

| Therapy | Aptamer | Target | Nanoparticle | Findings |
|---|---|---|---|---|
| Vinorelbine | AS1411 (DNA) | Nucleolin | PLGA-PEG | In vitro (MDA-MB-231, MCF-10a) internalization/cell viability (Zhou et al. (2014) *J Drug Target* 22(1): 57-66) |
| Curcumin | EpCAM (RNA) | Epithelial cell adhesion molecule | PLGA-lecithin-PEG | In vitro (HT29, HEK293) internalization/cell viability (Li et al. (2014) *Int J Nanomedicine* 9: 1083-96) |
| Daunorubicin | MUC-1 (DNA) | Mucin-1 | NIR-CuInSn$_2$ Quantum Dots | In vitro (MUC-1+ PC-3M, HepG2) internalization/cell viability (Lin et al. (2014) *Anal Chim Acta* 818: 54-60) |
| siRNA delivery | AS1411 (DNA) | Nucleolin | PEG liposome | In vitro (A375, HEK293) internalization/cell viability In vivo (NUDE BALB/c) tissue biodistribution, antitumor effects (Li et al. (2014) *Biomaterials* 35(12): 3840-50) |
| SN-38 (irinotecan metabolite) | MUC-1 (DNA) | Mucin-1 | Chitosan | In vitro (MUC-1+ HT-29, CHO) internalization/cell viability (Sayari et al. (2014) *Int J Pharm* 473(1-2): 304-15) |
| Doxorubicin & TMPyP$_4$ | AS1411 (DNA) | Nucleolin | Gold (Au) | In vitro (HeLa, MCF-7, MCF-7R) internalization/cell viability (Shiao et al. (2014) *ACS Appl Mater Interfaces*) |
| Docetaxel & Cisplatin | A10 (RNA) | Prostate specific membrane antigen | PLGA-PEG | In vitro (PSMA+ LNCaP cells) internalization/cell viability (Kolishetti et al. (2010) *Proc Natl Acad Sci USA* 107(42): 17939-44) |
| Bcl-xL shRNA & Doxorubicin | A10 (RNA) | Prostate specific membrane antigen | PEI-PEG | In vitro (PSMA+ LNCaP cells) internalization/cell viability (Kim et al. (2010) *Biomaterials* 31(16): 4592-9) |

In certain embodiments, the invention encompasses a pharmaceutical composition comprising the aptamers of the present invention and a pharmaceutically acceptable carrier. The term "pharmaceutical composition" refers to the combination of an active agent with a carrier, inert or active, making the composition especially suitable for diagnostic or therapeutic use in vivo or ex vivo. The carrier in the pharmaceutical composition must be acceptable in the sense that it is compatible with the active ingredient and capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate.

Another aspect of the present invention provides a method of delivering a therapeutic agent to an ovarian tumor cell in a subject in need thereof comprising administering to the subject an aptamer of the present invention, wherein the aptamer is conjugated to a therapeutic agent, and the aptamer localizes and binds to an ovarian tumor cell, resulting in internalization of the aptamer.

Yet another aspect of the present invention provides a method of treating ovarian cancer in a subject in need thereof comprising administering to a subject a therapeutically effective amount of an aptamer comprising the nucleotide sequence CTCCTCTGACTGTAACCACG-N$_x$-GCAT-AGGTAGTCCAGAAGCCA (SEQ ID NO: 9), wherein N is a nucleotide selected from the group consisting of G, C, A, or T; x is 19 or 20 nucleotides; the aptamer selectively binds to an ovarian tumor cell, the aptamer is conjugated to a therapeutic agent, and the aptamer localizes and binds to an ovarian tumor cell, resulting in internalization of the aptamer.

The terms "treating" or "treatment" as used herein refers to both therapeutic treatment and prophylactic or preventative measures. It refers to preventing, curing, reversing, attenuating, alleviating, minimizing, suppressing, or halting the deleterious effects of a disease state, disease progression, disease causative agent (e.g., bacteria or viruses), or other abnormal condition.

Yet another aspect of the present invention provides a method of diagnosing ovarian cancer in a subject in need thereof comprising contacting ovarian tissue sample with an aptamer of the present invention conjugated to a diagnostic agent; and detecting a signal generated by the diagnostic agent to indicate the presence of an epithelial ovarian tumor cell.

As used herein, the term "diagnose" refers to identify the nature of a medical condition of a subject, such as ovarian cancer, from its signs and symptoms.

As used herein, the term "therapeutically effective amount" generally refers to an amount of the aptamer to affect a desired biological response. Such response may be a beneficial result, including, without limitation, amelioration, reduction, prevention, or elimination of symptoms of a disease or disorder. Therefore, the total amount of each active component of the aptamer or method is sufficient to demonstrate a meaningful benefit in the patient, including, but not limited to, treatment of ovarian cancer. A "therapeutically effective amount" may be administered through one or more preventative or therapeutic administrations. When a therapeutically effective level" is applied to a single ingredient, administered alone, the term refers to that composition alone. When applied to a combination, the term refers to combined amounts of the active compositions that produce the therapeutic effect, whether administered in combination, consecutively, or simultaneously. The exact amount required will vary from subject to subject, depending, for example, on the species, age, and general condition of the subject; the severity of the condition being treated; the particular antigen of interest; in the case of an immunological response, the capacity of the subject's immune system to synthesize antibodies, for example, and the degree of protection desired; and the mode of administration, among other factors. An appropriate "effective" amount in any individual case may be determined by one of ordinary skill in the art. Thus, a "therapeutically effective amount" will typically fall in a relatively broad range that can be determined through routine trials.

The therapeutic aptamer compositions described herein may be administered by any suitable route of administration. In certain embodiments, the therapeutic aptamer compositions is administered intravenously, subcutaneously, transdermally, intradermally, intramuscularly, orally, transcutaneously, intraperitoneally (IP), or intravaginally.

As used herein, the terms "patient," "individual," or "subject" are used interchangeably and intended to include human and non-human animals. Exemplary human subjects include a human patient suffering from ovarian cancer, and EOC in particular. The term "non-human animals" includes all vertebrates, e.g., non-mammals (such as chickens, amphibians, reptiles) and mammals, such as non-human primates, domesticated and/or agriculturally useful animals (such as sheep, dogs, cats, rabbits, cows, pigs, etc.), and rodents (such as mice, rats, hamsters, guinea pigs, etc.).

The following examples are offered by way of illustration and not by way of limitation.

Example 1: Generation of Ovarian Tumor Cell-Specific Aptamers for Diagnostic and Therapeutic Uses To identify epithelial ovarian cancer cell-specific aptamers, modified whole Cell-SELEX was utilized to identify aptamers that distinguish between neoplastic epithelial cells and non-transformed epithelial cells. Target-specific DNA aptamers that bind and internalize into human Caov-3 ovarian epithelial adenocarcinoma cells (Zhan et al. (2013), *Bind Du Xue Bao* 29:573-77; Daniels et al. (2003) *Proc Natl Acad Sci USA* 100:15416-21) were identified with no prior knowledge of target molecules.

Cell Lines.

The Caov-3 adenocarcinoma cell line corresponds to late stage ovarian epithelial cancer and has been shown to express upregulated tumor biomarkers such as NB/70K, Ca-1, carcinoembryonic antigen (CEA), and Ba-2 (Buick et al. (1985) *Cancer Res* 45:3668-76). The human ovarian adenocarcinoma cell lines Caov-3 (HTB-75), SK-OV-3 (HTB-77), and SW626 (HTB-78) were obtained from ATCC (Manassas, Va.) and maintained in tissue culture 37° C. 5% $CO_2$. Caov-3 cell lines were maintained in Dulbecco's minimal essential medium (DMEM, GIBCO) supplemented with 10% fetal bovine serum (FBS, GIBCO) and 1% penicillin-streptomycin (GEMINI). SK-OV-3 cell lines were maintained in McCoys 5a media (ATCC) supplemented with 10% FBS (heat-inactivated, GIBCO), 1% penicillin-streptomycin (GEMINI). SW626 cell lines were maintained in Leibovitz media (ATCC) supplemented with 10% FBS (heat-inactivated, GIBCO), 1% penicillin-streptomycin (GEMINI), and 1% sodium bicarbonate (7.5% w/v, Cellgro). The pancreatic carcinoma cell line Hs766T (ATCC, HTB-134) and Suit-2 (Iwamura et al. 1987), human cervical adenocarcinoma HeLA (ATCC, CCL-2), breast adenocarcinoma cell lines MCF-7 (ATCC, HTB-22) and MDA-MB-231 (ATCC, CRM-HTB-26), murine embryonic fibroblast NIH/3T3 (ATCC, CRL-1658) were all maintained in DMEM supplemented with 10% FBS (heat-inactivated, GIBCO), 1% penicillin-streptomycin (GEMINI). Normal epithelial cell lines HEK-293 (ATCC, CRL-1573) maintained in DMEM supplemented with 10% FBS (heat-inactivated, GIBCO), 1% penicillin-streptomycin (GEMINI). The HPV immortalized human ovarian epithelial (HOSE 6-3) cells (Tsao et al. (1995) *Exp. Cell Res.* 218:499-507) maintained in Medium 199/MCDB105 media (1:1, Sigma Aldrich) supplemented with 10% FBS (heat-inactivated, GIBCO), 1% penicillin-streptomycin (GEMINI), 1% sodium bicarbonate (7.5% w/v, Cellgro).

Whole Cell-SELEX (Systematic Evolution of Ligands by Exponential Enrichment).

Aptamers were identified from an initial randomly generated ssDNA 60/61 base pair oligonucleotide library in a dual positive and negative selection process consisting of selection rounds followed with PCR enrichment prior to the subsequent round (FIG. 1). An HPLC-purified ssDNA aptamer library (Integrated DNA Technologies (IDT)) contained a centralized random sequence of 19 or 20 nucleotides flanked by fixed 5' 20 nucleotide sequences and fixed 3' 21 nucleotide sequences for PCR enrichment (5'-CTCCTCTGACTGTAACCACG-$N_x$-GCAT-AGGTAGTCCAGAAGCCA-3') (SEQ ID NO: 9). 2 μL of the aptamer library (100 μM) in TE was added to 8 μL $H_2O$ with target Caov-3 cells. Samples were denatured at 95° C. for 5 minutes and cooled on ice for 5 minutes before treating target cells. Cooled suspension were added to 980 μL binding buffer (BB, PBS (GIBCO) supplemented with 1% w/v Bovine Serum Albumin (BSA, Cellgro), 4.5 g/L glucose (Sigma Aldrich), 5 mM $MgCl_2$ (Sigma Aldrich). Aptamers were incubated on a monolayer of Caov-3 cells (seeded at $2.0 \times 10^6$ 48 hours prior, 37° C. 5% $CO_2$) in T25 flask at 4° C. for 30 minutes under constant agitation in the absence of competitor. After washing with PBS (3×) for 1 minute, adhesive cells were collected. Cells with aptamers were centrifuged 12,000 rpm for 2 minutes in microcentrifuge.

The supernatant was discarded and bound aptamers were eluted at 95° C. for 5 min in 50 μL 1×PBS.

To ensure aptamer target cell specificity, eluted aptamers were collected, resuspended in 950 μL BB and used for rounds negative selection against human papilloma virus (HPV) immortalized human ovarian surface epithelial cells HOSE 6-3 cells. Morphologically HOSE 6-3 cells exhibited structurally identical cytoskeleton filaments with that of normal ovarian epithelial cells and show no up-regulation of known ovarian tumor specific markers such as CA-125 after immortalization (Tsao et al. 1995). The non-transformed immortalized HOSE 6-3 cell line has demonstrated to be non-tumorigenic when inoculated into nude mice after 20 passages (Tsao et al. 1995). The use of HOSE 6-3 cells for negative selection was deemed significant for potential in vivo therapeutic applications in which aptamers would need to bind to malignant cells but not to neighboring non-tumor cells of otherwise similar cell type or origin.

The HOSE 6-3 cells were seeded at $2.0 \times 10^6$ 48 hours prior, 37° 5% $CO_2$ in T25 flask 4° C. 30 minutes under constant agitation in the absence of competitor (Tsao et al. 1995). 1 mL of BB was collected and aptamers eluted by ethanol precipitation resuspended in 20 μL TE. The collected aptamers were amplified by PCR (GE HEALTHCARE illustra PuReTaq Ready-To-Go PCR beads): Primer A: 5'-gaggagactgacattggtgc (SEQ ID NO: 10), Primer B: cgtatccatcaggtcttcgga-5' (SEQ ID NO: 11), Cycle: 94° C. 5 minutes, (35 cycles) 94° C. 30 seconds, 62° C. 30 seconds, and 72° C. 45 seconds, followed by elongation 72° C. 10 minutes. PCR product was concentrated using DNA Clean & Concentrator™-5 (Zymo Research) and the total volumes of recovered aptamers were used for proceeding rounds of selection. Concentrations, as detected by NanoDrop, were significantly less than initial starting concentration at the conclusion of round 1. Subsequent treatment concentration of aptamers was maintained (~100 ng) following elution of aptamers and PCR enrichment.

Negative selection was performed at rounds 3, 5, 7, 9, 11, and 13 which promoted identification of aptamers highly specific to malignant cells. The first and second rounds of SELEX did not utilize the counter selection step, but were introduced during the $3^{rd}$, $5^{th}$, $7^{th}$ and subsequent odd rounds of selection. A total of 15 rounds of whole-cell SELEX were performed on the target cell line. Wash strength was enhanced gradually from 1 to 2 minutes and flask sizes increased from T25 to T75 following and including round 10 of positive selection.

TOPO Cloning

In order to confirm that full-length aptamers were being selected for and enriched through consecutive rounds, TOPO cloning was used. Complete 60mer aptamer sequences were identified after rounds 3, 8, and 12 of whole Cell-SELEX. To monitor the presence of aptamers through rounds of selection, aptamers from rounds 3, 8, and 12 were cloned into *Escherichia coli* by manufacturers' recommendations using a One Shot TOPO10A cloning kit (Invitrogen) then analyzed by Sequetech DNA Sequencing Service (Mountain View, Calif.). Global sequence panels were obtained after 15 rounds of selection by Ion Torrent Next Generation Sequencing (University of North Carolina-Charlotte).

Clones analyzed from round 3 showed 11 distinct aptamer species with one subgroup representing 67% of the population. Sequencing of clones from round 12 of selection provided 10 distinct aptamer species with one of these aptamer species representing 33% of the sequenced population.

Figure 2:
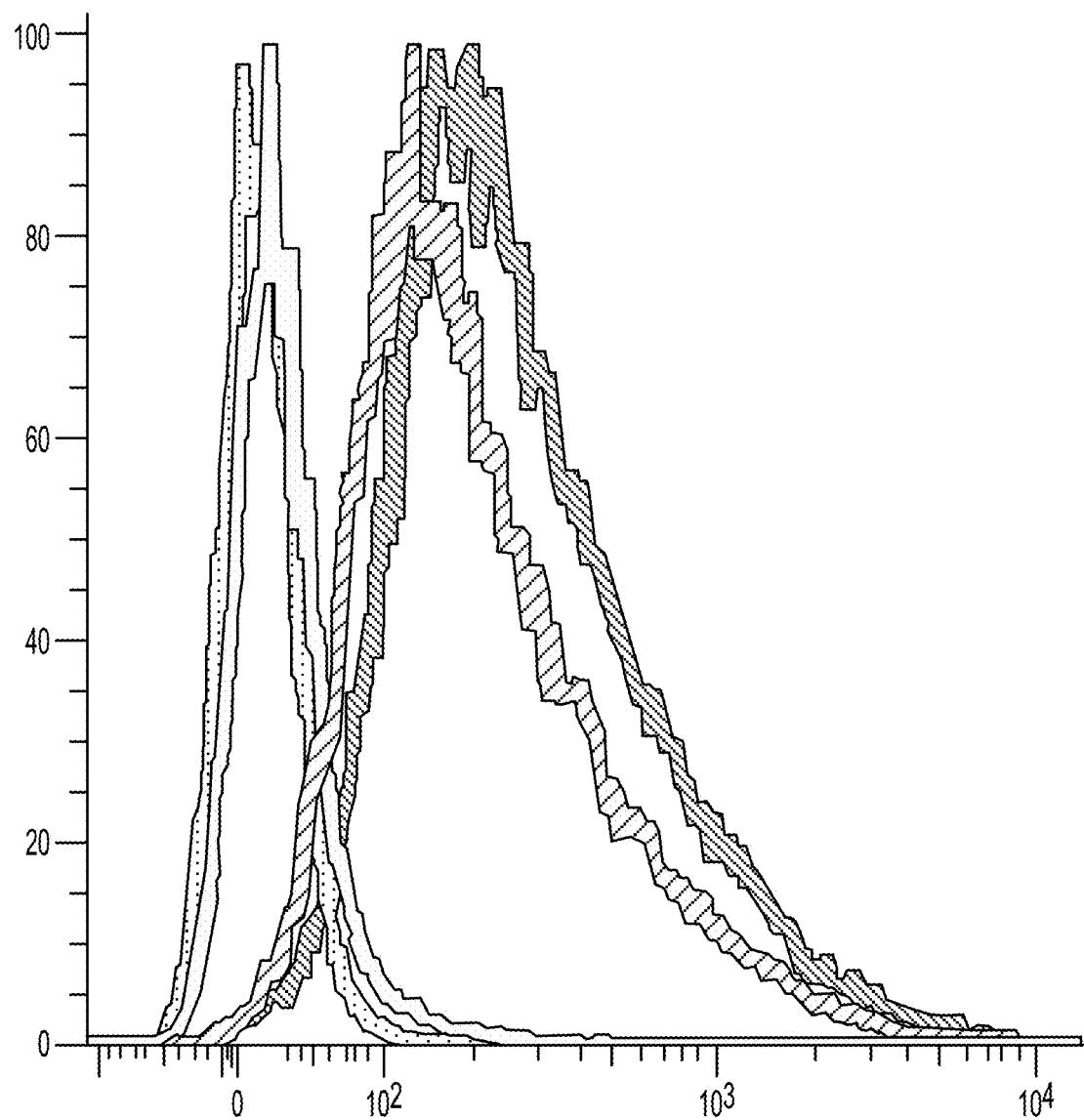
FIG. 2 is a graph showing flow cytometry histograms for Cy5-labeled aptamer pools from successive rounds of Cell-SELEX. A right shift in fluorescence of the cell populations is indicative of increases in aptamer binding and internalization. Aptamer rounds of selection: initial random library (dotted line), round 3 (white line), round 8 (large stripes) and round 12 (small stripes) of Cell-SELEX.

Additionally, the enrichment process was also monitored by way of flow cytometry with Cy5 labeled aptamers. Aptamers were amplified from indicated rounds of Cell-SELEX by PCR using a 5'-Cy5 labeled primer and an anti-sense 5'-biotin labeled primer, as shown in FIG. 2. The removal of the 60mer aptamer anti-sense strands was done by denaturing the double stranded PCR product (95° C. 5 minutes) and isolating biotin labeled strands with streptavidin with subsequent exposure to a magnetic field. This ensured that the remaining supernatant was rich with Cy5 labeled aptamers. The Cy5 labeled aptamers (100 ng) were incubated with target Caov-3 cells, collected by scraping, and analyzed by flow cytometry. Baseline fluorescent values were determined using a Cy5 labeled initial random library. A right shift in the fluorescent cell population can be seen when fluorescently labeled aptamers from rounds 3, 8, and 12 of Cell-SELEX were incubated with Caov-3 cells (FIG. 2). This shift in fluorescent populations indicates enrichment of cell specific aptamers that bind and internalize into cells. Moreover, the observed difference in Cy5 fluorescently labeled Caov-3 cell populations significantly increases when comparing aptamer pools from round 3 to round 8 of Cell-SELEX (FIG. 2). The observed shift in fluorescently labeled Caov-3 cell populations seen between round 8 and round 12 aptamer pools is significantly less which suggests that aptamer pools are nearing the threshold of potential aptamer enrichment.

Next Generation Ion Torrent Sequencing.

In order to characterize the complete aptamer population, Next-Generation Ion Torrent (NGIT) sequencing was used. 100 ng dsDNA PCR products were confirmed by Quant-iT™ PicoGreen® dsDNA Assay Kit (Invitrogen) and were used as template in the Ion Xpress Plus Fragment Library Kit (Invitrogen) following the protocol for short amplicons. Amplification of the prepared library was required; therefore the protocol to amplify and purify the library was followed. The amplified library was quantified using the Kapa Biosystems Library Quantification Kit for the Ion Torrent platform on a Bio-Rad MyIQ iCycler to determine the Template Dilution Factor (TDF) to be used with the Ion PGM Template OT2 200 Kit and the OneTouch 2 instrument. After emulsion PCR, the clonally amplified sample was run on the Ion Torrent PGM instrument using the Ion PGM Sequencing 200 Kit v2 and a 314 chip. Run conditions included 260 flows on the PGM instrument for sample 1 and 500 flows for sample 2.

53% loading efficiency resulting in over 293,000 ssDNA reads were obtained. From an initial random pool of approximately $4^{20}$ sequences, NGIT sequencing identified 7 full-length aptamers (Table 2) within the aptamer pool. Aptamers RLA01, RLA02, and RLA03 were selected for further studies. Given the flow cytometry data and the identification of seven unique aptamers in sequencing data from the initial randomized pool, the Cell-SELEX protocol was terminated after 15 rounds.

The unique aptamer sequences shown in Table 2 are set forth in the following nucleic acid sequences: RLA01 (SEQ ID NO: 1); RLA02 (SEQ ID NO: 2); RLA03 (SEQ ID NO: 3); RLA04 (SEQ ID NO: 4); RLA05 (SEQ ID NO: 5); RLA06 (SEQ ID NO: 6); and RLA07 (SEQ ID NO: 7). The "Scrambled Aptamer" nucleic acid sequence is set forth in SEQ ID NO: 8. RLA01, RLA02, RLA03, RLA04, RLA05, RLA06, and RLA07 share the following nucleic acid sequence: CTCCTCTGACTGTAACCACG-$N_x$-GCAT-AGGTAGTCCAGAAGCCA (SEQ ID NO: 9), where each N represents any deoxyribonucleic acid (A, C, G, or T) and x represents a sequence of 19 or 20 nucleotides in length.

TABLE 2

Sequences of identified aptamers by Cell-SELEX specific for Caov-3 ovarian tumor cell lines.

| Aptamer | Sequence | SEQ ID NO: |
|---|---|---|
| RLA01 | CTCCTCTGACTGTAACCACGCGGAAAGCATCAGGGTTGAGCATAGGTAGTCCAGAAGCCA | SEQ ID NO: 1 |
| RLA02 | CTCCTCTGACTGTAACCACGAGAAGGTCCAGAGAGTAGTGGCATAGGTAGTCCAGAAGCCA | SEQ ID NO: 2 |
| RLA03 | CTCCTCTGACTGTAACCACGCTACGGTTCGGAGGACACCCGCATAGGTAGTCCAGAAGCCA | SEQ ID NO: 3 |
| RLA04 | CTCCTCTGACTGTAACCACGCGAGGGGCGGACAGGGGAGGCATAGGTAGTCCAGAAGCCA | SEQ ID NO: 4 |
| RLA05 | CTCCTCTGACTGTAACCACGGATCAGGGGAAACTCCAGTGGCATAGGTAGTCCAGAAGCCA | SEQ ID NO: 5 |
| RLA06 | CTCCTCTGACTGTAACCACGTGACTAATTAGAGGTGGATCGCATAGGTAGTCCAGAAGCCA | SEQ ID NO: 6 |
| RLA07 | CTCCTCTGACTGTAACCACGTTATGAATTGGCGCCGGGGAGCATAGGTAGTCCAGAAGCCA | SEQ ID NO: 7 |
| Scrambled Aptamer | ACTCAACGAACGCTGTGGATGCGACATAGCTAGCAGCGCATATGTATGTACATGGACATCT | SEQ ID NO: 8 |

In order to be most physiologically relevant for future therapeutic uses, aptamers should interact with the target malignant cells and not other non-malignant cells which would be neighboring cells and likely of the same original cell origin. Notably, the adapted Cell-SELEX protocol included negative selection against non-malignant ovarian epithelial cells. Flow cytometry and confocal analysis supported non-reactivity of the aptamers to non-malignant epithelial cells of both ovarian and kidney origin. By contrast, others utilized HeLa cells, a known neoplastic immortalized line for negative selection (Van Simaeys et al. (2010) *PloS One* 5:e13770). That the protocol described herein yielded aptamers unique from those previously reported highlights that individual Cell-SELEX strategies used will be a key factor in determining what aptamers are identified. Large bioinformatics approaches for comparison of multiple parallel aptamer pools and a large panel of cell types would reveal similar sequence patterns for aptamers that bind to related disorders.

In conclusion, whole Cell-SELEX was modified to identify seven DNA-based aptamers that bind with high affinity to the EOC cell line Caov-3 but importantly not to the non-malignant epithelial HOSE 6-3 cell line. The modified protocol described here is unique in that EOC aptamers were identified that are specific to Caov-3 following negative selection against a non-transformed epithelial cell line. Following identification by SELEX, additional assays were performed on the 7 aptamers to assess their biologic activity in ovarian tumor cells.

Example 2: Binding Capacity of Ovarian Tumor Cell-Specific Aptamers

Flow cytometry was used to quantify aptamer binding activity. RLA01, RLA02, RLA03, RLA04, RLA05, RLA06 and RLA07 were evaluated to determine the binding kinetics of each and calculate apparent equilibrium dissociation constants ($K_d$).

Flow Cytometry (Binding Kinetics).

RLA01, RLA02, RLA03, RLA04, RLA05, RLA06, and RLA07 were obtained from IDT labeled with a cyanine dye Cy5 fluorescent dye on the 5' end to enable detection by flow cytometry and quantify the number of cells that bind to the target aptamer. Additionally, a random scrambled aptamer conjugated to Cy5 was used as a negative control to demonstrate specificity (Table 2).

Target EOC Caov-3 cells as well as EOC cell lines SK-OV-3 and SW626 were treated with increasing molar concentrations of Cy5-aptamers for 2 hr. The binding affinity of aptamers was determined by incubating cell lines on 6-well plates (seeded at $1.0 \times 10^6$, incubated 48 hours) with varying concentrations of Cy5 labeled aptamer. 25 µL aptamer pool in TE was added to 1 mL of cell line specific media and incubated at 37° C. 5% $CO_2$ 2 hours agitating slightly every 30 minutes. Cells were then washed twice with 2 mL 1×PBS, scraped in 1 mL 1×PBS, and filtered through a 35 µm nylon mesh cell strainer polystyrene tube (BD Falcon).

Following washing of excess unbound aptamer, cells were analyzed by flow cytometry to quantify Cy5 fluorescence. Cells were subjected to flow cytometric analysis within 1 min and fluorescent events were determined with a Becton Dickinson LSRFortessa Flow Cytometer by counting 50,000 events. A Cy5 labeled randomized unselected 60mer oligonucleotide was used as negative control. Mean fluorescent events (n=3) were recorded and used to calculate an apparent dissociation constant ($K_d$) for specific binding. The $K_d$ of the fluorescent aptamers were obtained by fitting the dependence of fluorescence intensity of specific binding on the concentration of the ligands to the equation $Y = B_{max} * X^h / (K_d^h + X^h)$ using GraphPad Prism software (La Jolla, Calif.). When calculating respective $K_d$ values baseline fluorescence for untreated cells was not pre-subtracted off since detected initial auto fluorescence made no significant impact on the calculated $K_d$ values. Concentrations of Cy5-aptamer conjugates were brought to 1600 nM to saturate the system and obtain sigmoidal curves giving the most accurate $K_d$ values for post hoc analysis.

Figure 3A:
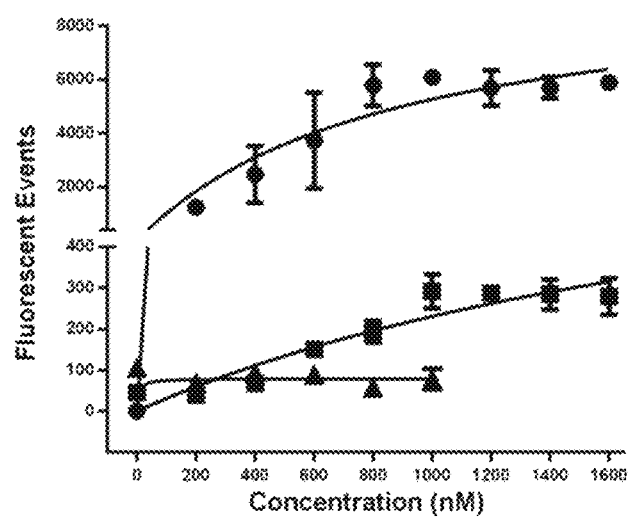
FIG. 3A-3C shows graphs of binding kinetics of ovarian tumor specific aptamers used to determine equilibrium dissociation constants ($K_d$) to ovarian tumor cell lines. On each graph, a circle symbol represents the ovarian epithelial malignant cell lines Caov-3 (●), a square symbol represented the SK-OV-3 cells (■), and a triangle symbol represents the SW626 cells (▲). Data points represent the average fluorescent events observed (n=3, error bars±SD) at indicated nM concentrations as quantified by flow-cytometry.
Figure 3B:
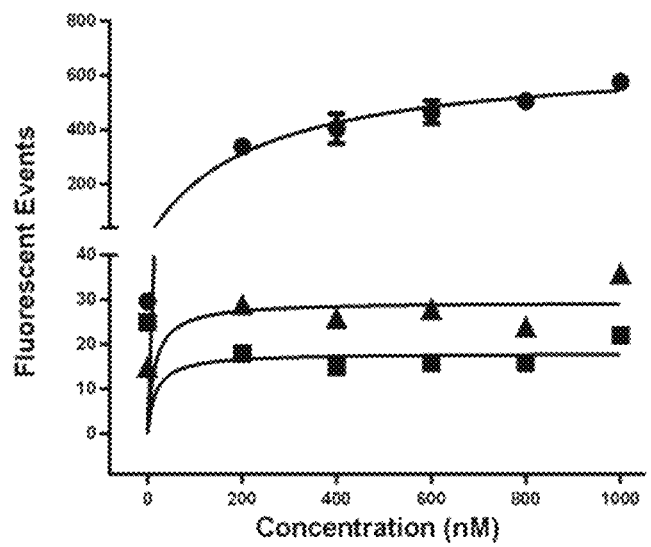
Figure 3C:
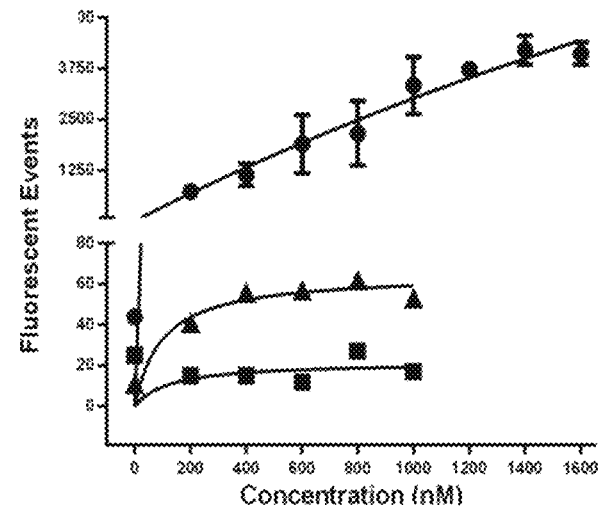

To establish baseline fluorescence, untreated Caov-3 cells were also analyzed and gating of the background fluorescence was set to 0.01% of the total population analyzed. As expected, no fluorescent events above the background gate were observed when Caov-3 cells were incubated with the random scrambled aptamer at concentrations (1 nM to 1.6 µM). As shown in FIG. 3, RLA01, RLA02, and RLA03 all demonstrated a dose-dependent increase (1 nM to 1.6 µM) in binding to target Caov-3 cells as demonstrated by the increased number of fluorescent events (FIG. 3A, FIG. 3B, FIG. 3C, closed circles, respectively). Binding of each of the aptamers to Coav-3 cells was highly specific since minimal binding events were detectable by flow cytometry when any were incubated with either of the analogous epithelial ovarian tumor cell lines SK-OV-3 or SW626 (FIG. 3). Similar to Caov-3, SK-OV-3 cells are derived from epithelial ovarian adenocarcinoma, but also characterized as resistant to multiple cytotoxic drugs (Abouzeid et al., (2014) Int. J. Pharm. 464:178-184). Although SW626 was isolated as an ovarian adenocarcinoma, genome expression evidence recently indicated it likely originated as a colorectal tumor metastasized to the ovary (Furlong et al., (1999) J. Natl. Cancer Inst. 91:1327-1328). From the flow cytometry data shown in FIG. 3, respective apparent $K_d$ values for RLA01, RLA02, and RLA03 to Caov-3 cells were calculated in the nanomolar range as 365.3±24.14 nM, 225.5±48.29 nM, and 505±70.64 nM, respectively (Table 3). The respective apparent $K_d$ values for RLA04, RLA05, RLA06 and RLA07 to Caov-3 cells were also calculated in the nanomolar range by the same method as RLA01-RLA03. The $K_d$ value for RLA04 was calculated as 385.8±60.3 nM. The $K_d$ value for RLA05 was calculated as 670.0±90.1 nM. The $K_d$ value for RLA06 was calculated as 481.5±84.2 nM. The $K_d$ value for RLA07 was calculated as 330.1±54.3 nM.

cell lines (FIG. 4D), and apparent $K_d$ values of 627.1±65.67 nM and 645.3±60.91 nM were determined (Table 3). This type of analysis demonstrates that the aptamers RLA01-07 have apparent Kd values in the nano molar range. Although flow cytometry confirms aptamer-cell binding for both HeLa and SK-OV-3 cell lines, the average fluorescent events observed were significantly less for both when compared to RLA01 binding to Caov-3 cells and showed no interaction with the scrambled aptamer at equal doses, as shown in FIG. 4D.

Specificity of RLA01, RLA02, and RLA03 was further demonstrated with a large panel of immortalized non-malignant epithelial and multiple malignant epithelial cell lines including two malignant pancreatic epithelial carcinomas (Suit-2, Hs766t), two mammary epithelial adenocarcinomas (MCF-7, MDA-MB-231), one cervical epithelial adenocarcinoma (HeLa), two ovarian epithelial adenocarcinoma cell lines (SK-OV-3, SW626), as well as kidney epithelial cells (HEK293), and murine fibroblast NIH/3T3 cells. Kidney epithelial tissue was chosen because kidneys play a major role in removal of organic waste from the bloodstream thus would impact potential clinical use by intravenous delivery of aptamers. Aptamer-binding events were minimal or undetectable as shown by flow cytometry when incubated with malignant cell lines in increasing molar concentrations (Table 3). As shown in FIG. 4B, binding of aptamers was also time dependent. Increasing incubation time of Cy5-RLA01 with Caov-3 cells from 2 hours to 4 hours produced 275% more fluorescent events while fluorescent events in HOSE 6-3 cells remained similar to baseline controls (FIG. 4B).

TABLE 3

Characterization of identified Caov-3 aptamer binding kinetics with target and non-target cells.

| | Ovarian | | | Normal | | Breast | | | | | |
|---|---|---|---|---|---|---|---|---|---|---|---|
| | Caov-3 | SK-OV-3 | SW626 | HEK293 | HOSE 6-3 | Cervical HeLa | MDA-MB-231 | MCF-7 | Pancreatic Suit-2 | Hs766t | Murine NIH3T3 |
| RLA01 | +++ 365.3 ± 24.14 | + 627.1 ± 65.67 | − | − | − | + 645.3 ± 60.91 | − | − | − | − | − |
| RLA02 | + 225.5 ± 48.29 | − | − | − | − | − | − | − | − | − | − |
| RLA03 | ++ 505 ± 70.64 | − | − | − | − | − | − | − | − | − | − |

Figure 4A:
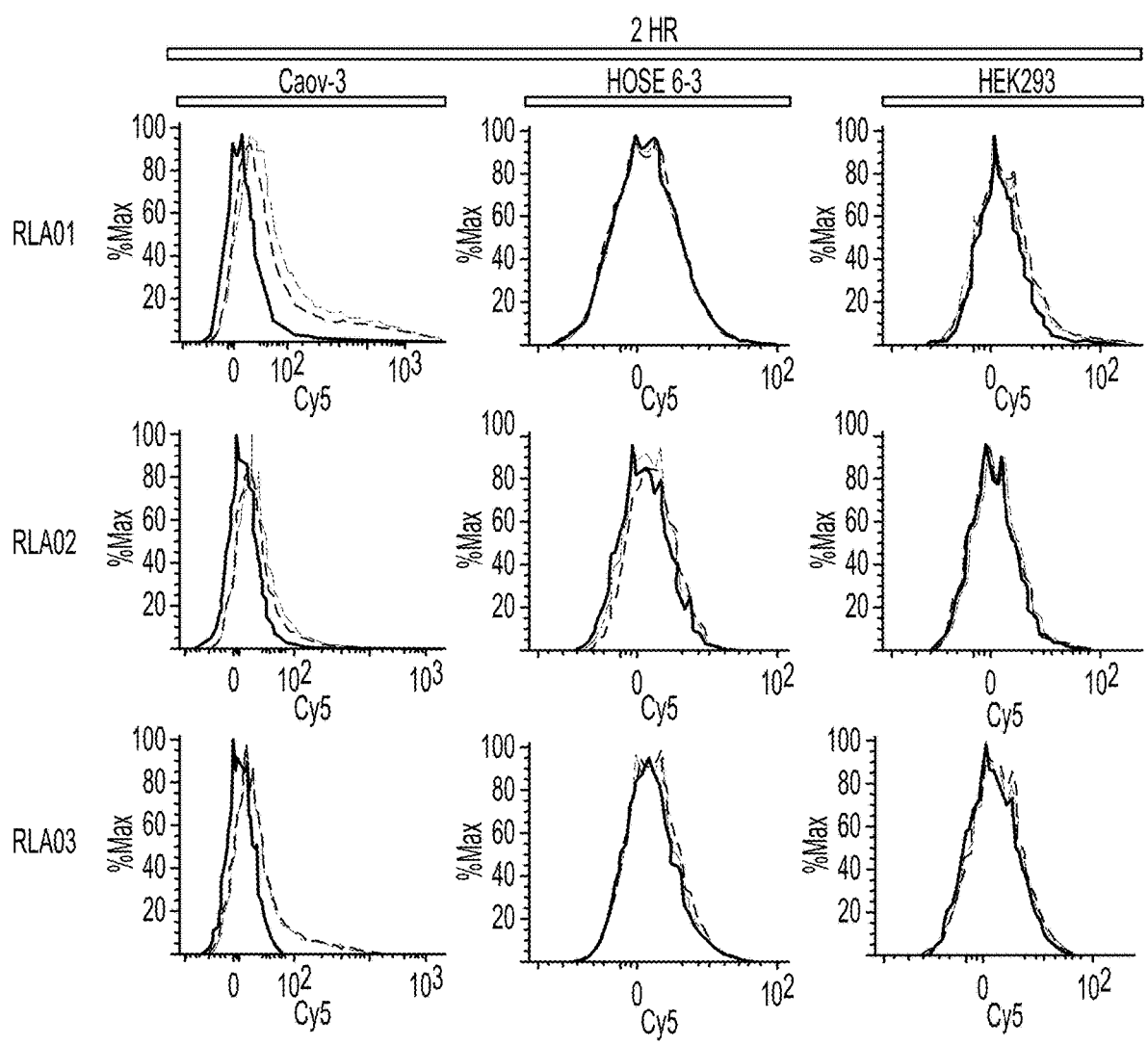
FIG. 4A-4D shows the dose-dependent and time-dependent specificity of RLA01, RLA02, and RLA03 aptamers binding to normal and target cells.
Figure 4B:
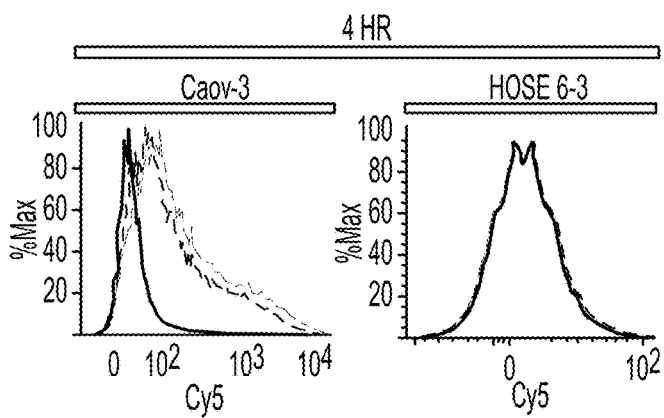
Figure 4C:
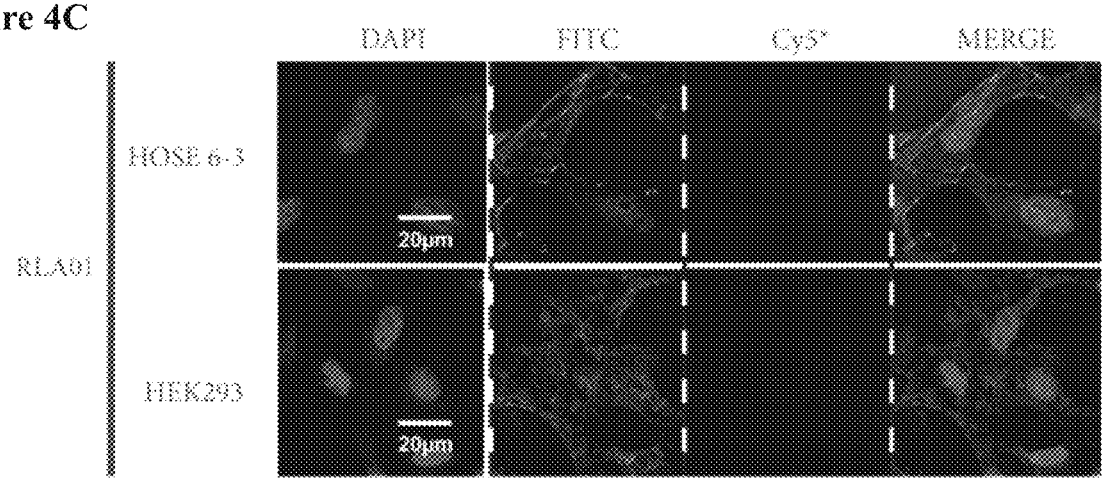
Figure 4D:
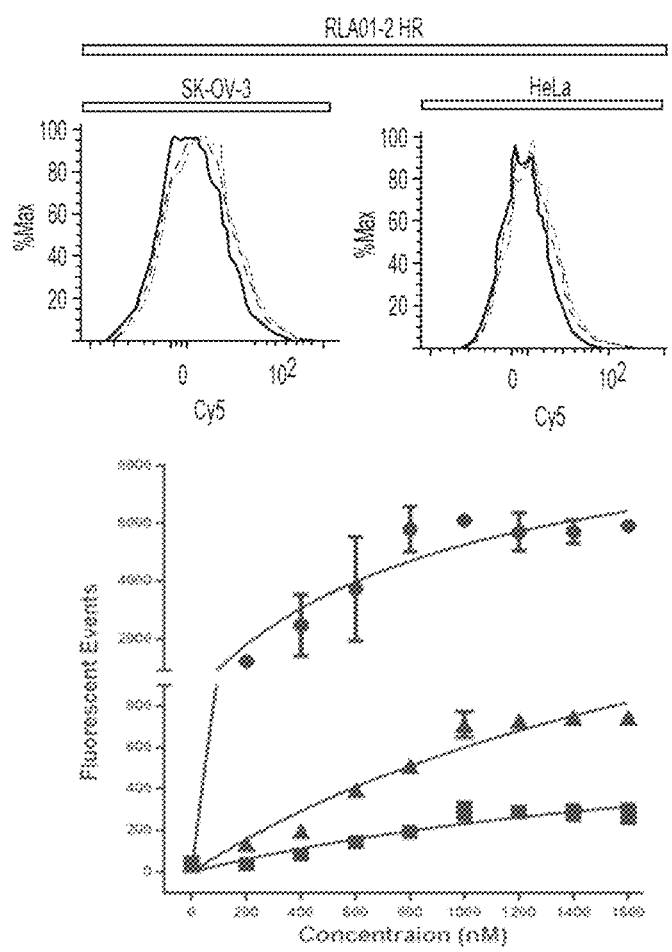

$K_d$ = nM
+++: >15% of total cell population showing Cy5 fluorescent events
++: 10%-15% of total cell population showing Cy5 fluorescent events
+: <10% of the total cell population showing Cy5 fluorescent events
−: <1% of total cell population showing Cy5 fluorescent events-$K_d$ undetermined Aptamer specificity was further demonstrated by comparison of Cy5-aptamer binding to a large panel of cell lines, as shown in FIG. 4A. Incubation with both 400 nM (represented by a "--- - ---" line in FIG. 4A) and 800 nM (represented by a "- - -" line in FIG. 4A) Cy5-RLA01 for 2 hours produced a right shift in the fluorescent Caov3 cell population over untreated cells, consistent with an increase in aptamer-cell interaction. By contrast minimal shift of the population above baseline was observed with either non-transformed HOSE 6-3 cells or kidney epithelial HEK293 cells when incubated with increasing molar concentrations of Cy5-RLA01, Cy5-RLA02, or Cy5-RLA03 (FIG. 4A). This was further demonstrated by confocal microscopy as seen in FIG. 4C. Aptamer-cell interactions were observed with Cy5-RLA01 when incubated with SK-OV-3 and HeLa These results demonstrate that aptamers RLA01, RLA02, and RLA03 bound with high affinity to the target Caov-3 cells used in the initial screen for their identification. RLA02 and RLA03 demonstrated exclusive specificity with minimal to undetectable interaction with any of the malignant or non-malignant epithelial cell lines tested except the target Caov-3 cells. RLA01 showed binding interactions with both SK-OV-3 and HeLa cells, as compared to controls. However, the max fluorescent events observed in the other cell lines were lower than the binding kinetics to Caov-3, which suggests the existence of a commonly shared receptor among the three cell lines expressed at highest levels in Caov-3 cells and moderate or low levels on the other two or structurally similar or related proteins are present on the membranes of the three cell lines with RLA01 having the highest binding affinity for the one that is expressed on Caov-3 cells. Ovarian surface epithelium and cells in the Müllerian tract are derived from common embryonic coelomic progenitors (Hennessy et al., 2009 *Lancet* 374:1371-1382). Since Caov-3 and SK-OV-3 cells were isolated from ovarian epithelial tissue it is likely that a common receptor is shared between the two cell lines. However, a study comparing EOC cell lines involving karyotyping, surface markers, and drug resistance indicated that Caov-3 cell lines display a unique genetic lesion on the long arm of chromosome 3 (del(3)(p13:) not seen in SK-OV-3 cell lines (Buick et al., (1985) *Cancer Res.* 45:3668-3676; Beaufort et al., (2014) *PLoS One* 9:e103988). This would result in altered morphology in common surface structures such as dysregulated glycosylation of common receptors on Caov-3 versus SK-OV-3 cells. Additionally, the heterogeneity observed in EOC development would further explain common expression of surface structures seen in ovarian tumor subtypes and cervical carcinomas which are known to originate from squamocolumnar junctions of the cervix (Herfs et al., (2012) *Proc. Natl. Acad. Sci. USA* 109:10516-10521). Data suggest that ovarian tumors manifest from cells expressing Müllerian tract differentiation. Although fallopian, ovarian, and pelvic cancers are treated as three distinct neoplastic diseases, it is believed that the majority of them originate from a common Müllerian progenitor and/or distal fimbrae tubes of the ovary (Dubeau, (2008) *Lancet Oncol.* 9:1191-1197; Hennessy et al., (2009) *Lancet* 374:1371-1382; Masiakos et al., (1999) *Clin. Cancer Res.* 5:3488-3499; Saad et al., (2010) *Horm. Cancer* 1:277-290; Crum et al., (2007) *Clin. Med. Res.* 5:35-44). It is possible that these malignant cell lines share a common receptor that is up- or down-regulated depending on particular context, abnormality, or in response to external stimuli such as hormones. SK-OV-3 cells originate from an epithelial adenocarcinoma similar to Caov-3 cells; however they also demonstrate levels of resistance to multiple cytotoxic drugs including platinum-taxanes (Buick et al., (1985) *Cancer Res.* 45:3668-3676; Abouzeid et al., (2014) *Int. J. Pharm.* 464:178-184) and thus would differ from Caov-3 at a minimum in their expression of ABC multiple drug resistance (MDR) transporters on the cell surface. However, similarity of characteristics of these cell lines is in their origin in the female reproductive tract rather than as epithelial cells per se since no binding events were detected by either flow cytometry or confocal imaging when RLA01 was incubated with epithelial cells from other tissues.

The seven aptamers have apparent $K_d$ values in the nanomolar range, which show that they bind with high affinity to target cells. Physiologically relevant apparent equilibrium dissociation values for therapeutic molecules are considered to be in the nanomolar to picomolar range. Initial dosing of pegaptanib (Macugen) to inhibit $VEGF_{165}$ in HUVEC cells had an $IC_{50}$ value between 0.75-1.4 nM with total inhibition of $VEGF_{165}$ binding observed at 10 nM (Bell et al., (1999) *In Vitro Cell Dev. Biol. Anim.* 35:533-542). However, pegaptanib is an inhibitory aptamer with a single agonist and was developed in a sequential process in the presence of a purified target molecule only (Ruckman et al., (1998) *J. Biol. Chem* 273:20556-20567). Another non-SELEX identified aptamer AS1411, formerly ARGO100, showed initial inhibition of MDA-MD-231 cell proliferation after a 15 µM dose (Bates et al., (1999) *J. Biol. Chem* 274:26369-26377; Ireson et al., (2006) *Mol. Cancer Ther.* 5:2957-2962). Several aptamers have been identified through positive and negative whole Cell-SELEX. The reported DOV-3 aptamer with an apparent $K_d$ 132±32 nM (Van Simaeys et al., (2010) *PLoS One* 5:e13770) identified as binding to Caov3 cells, similar to this study, was counter-selected against malignant cervical HeLa cells which may not be as relevant for identification of ovarian tumor specific aptamers. Additional whole Cell-SELEX aptamers with nanomolar $K_d$ values target Axl (GL21 aptamer apparent $K_d$ 221 nM) (Cerchia et al., (2012) *Mol. Ther.* 20:2291-2303), B-cell receptors of Burkitt's lymphoma cell lines (TD05 apparent $K_d$ 74.7±8.7 nM) (Mallikaratchy et al., (2011) *Nucleic Acids Res.* 39:2458-2469; Tang et al., (2007) *Anal. Chem.* 79:4900-4907), and liver cancer MEAR cell line (TLS6 apparent $K_d$ 157.0±16.9 nM) (Shangguan et al., (2008) *Anal. Chem.* 80:721-728).

In addition to apparent $K_d$ values in the nanomolar range, higher total fluorescent events over a range of aptamer doses supports use of these aptamers as attractive candidates to chaperone chemotherapeutic drugs or small molecule vehicles directly to tumor sites. The number of events observed by flow cytometry directly correlates to effective dose of aptamer-drug conjugates internalized. This would increase the efficacy of current treatment protocols by delivering more cytotoxic drugs to the tumor while reducing systemic cytotoxic side effects typically seen with them.

In sum, specificity of RLA01, RLA02, and RLA03 was shown across a panel of tumor types including breast, cervical, and pancreatic malignancies. Additionally, the differences in aptamer binding kinetics demonstrated here can be used to infer particular molecular characteristics of the target cells. The identified aptamers can be used to enhance the sensitivity of current clinical diagnostic tools to identify ovarian neoplasms. The lack of interactions observed with non-tumor epithelial cells demonstrates that aptamer-based therapies can minimalize interaction with non-malignant tissues and improve upon the incidence of false positive results regarding benign versus malignant diagnosis or to potentially deliver cytotoxic drugs to distal tumor sites in the body. Thus, these data suggest these aptamers are attractive candidates for further analysis to direct and localize chemotherapeutics to tumor sites and potentially aid in the early diagnosis of ovarian malignancies.

Example 3: Internalization of Ovarian Tumor Cell-Specific Aptamers

Specific binding and internalization of RLA01, RLA02, and RLA03 to Caov-3 cells was demonstrated by flow cytometry and confocal imaging, as shown in FIG. 5.

Flow Cytometry (Endosomal Internalization).

To determine the percent internalization of Cy5-aptamer conjugates pHrodo® Red Transferrin Conjugate was used (Invitrogen). Aptamers (500 nM) were added to 1 mL cell specific media and incubated on Caov-3 cells (6-well plates seeded at $1.0 \times 10^6$ 48 hours prior, 37° 5% $CO_2$) and observed at 30, 60, 90, and 120 minutes post treatment. 30 min before pre-determined time points staining with endosomal specific marker pHrodo® Transferrin Conjugate was done by the manufacturers' recommended protocol (25 µg/mL). Cells were then washed twice with 2 mL 1×PBS, scraped in 1 mL 1×PBS, and filtered through a 35 µm nylon mesh cell strainer polystyrene tube (BD Falcon). Cells were subjected to flow cytometric analysis within 1 min and fluorescent events were determined with a Becton Dickinson LSR-Fortessa Flow Cytometer by counting 100,000 events. Percent internalization was calculated by the following equation: (number of dual Cy5 pHrodo Red events—number of pHrodo Red untreated background)/number of Cy5 events.

Cell membranes were identified by Wheat Germ Agglutinin conjugates labeled with Alexa Fluor® 488 enabling identification of two key cellular structures: (i) the cell membrane where Cy5-aptamer conjugates are predicted to localize upon initial target recognition, and (ii) the internal endosomal membranes where aptamers are expected to localize to if efficiently internalized into cells. Images of aptamer specific binding and endosomal internalization were assessed as early as 30 min and up to 2 hours post initial treatment of Cy5-aptamer conjugates ranging in dosages of 1 µM to 25 µM. Supporting the flow cytometry data, no internalization at any dose was observed with scrambled aptamer (Table 2).

Figure 5D:
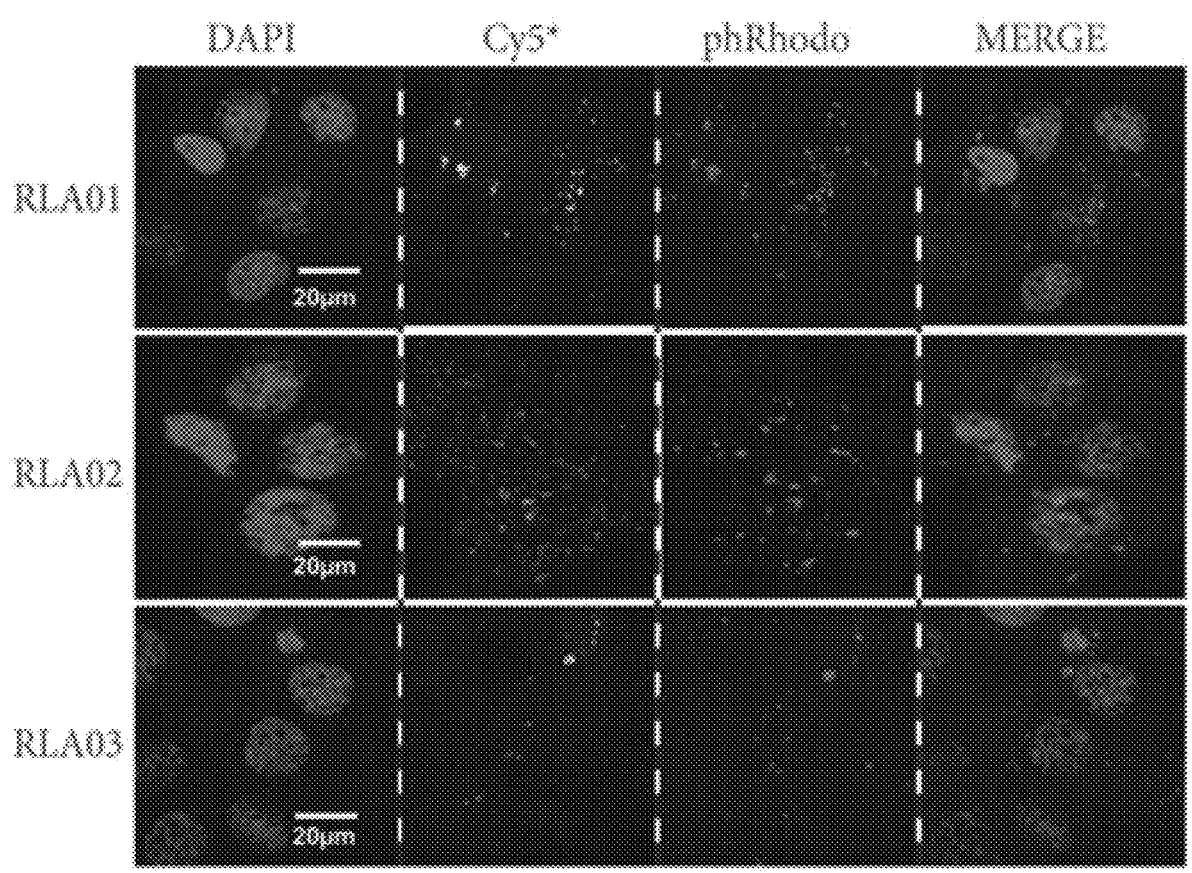
Figure 6A:
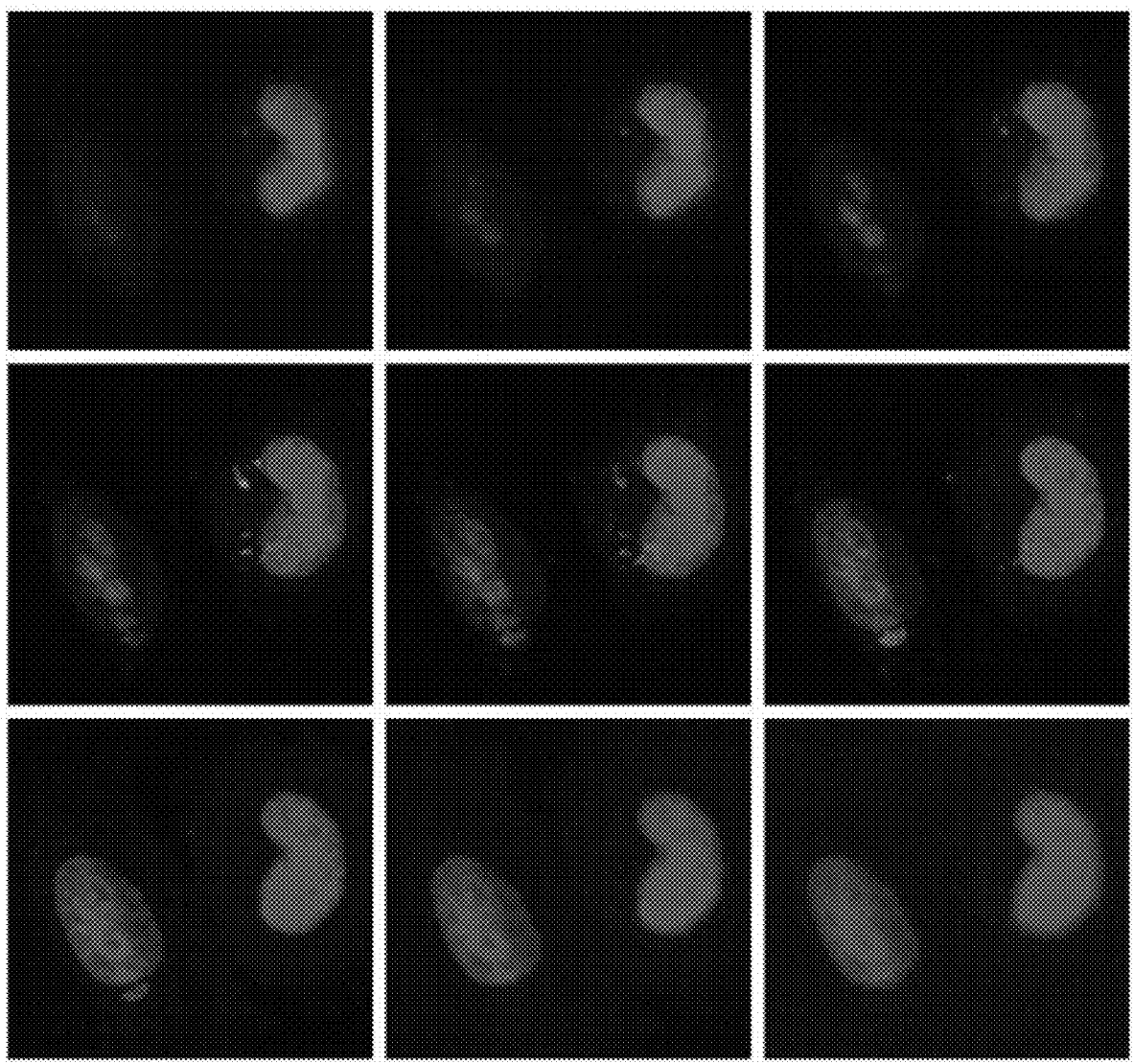
FIG. 6A-6B shows endosomal internalization of RLA01 as demonstrated by confocal microscopy z-stack imaging. Confocal imaging of Caov-3 cell lines treated with Cy5-RLA01 imaged at 60× using a nuclear stain (DAPI), endosomal specific marker pHrodo Red Transferrin Conjugate (rhodamine pseudo), and Cy5-aptamers (Cy5 pseudo).
Figure 6B:
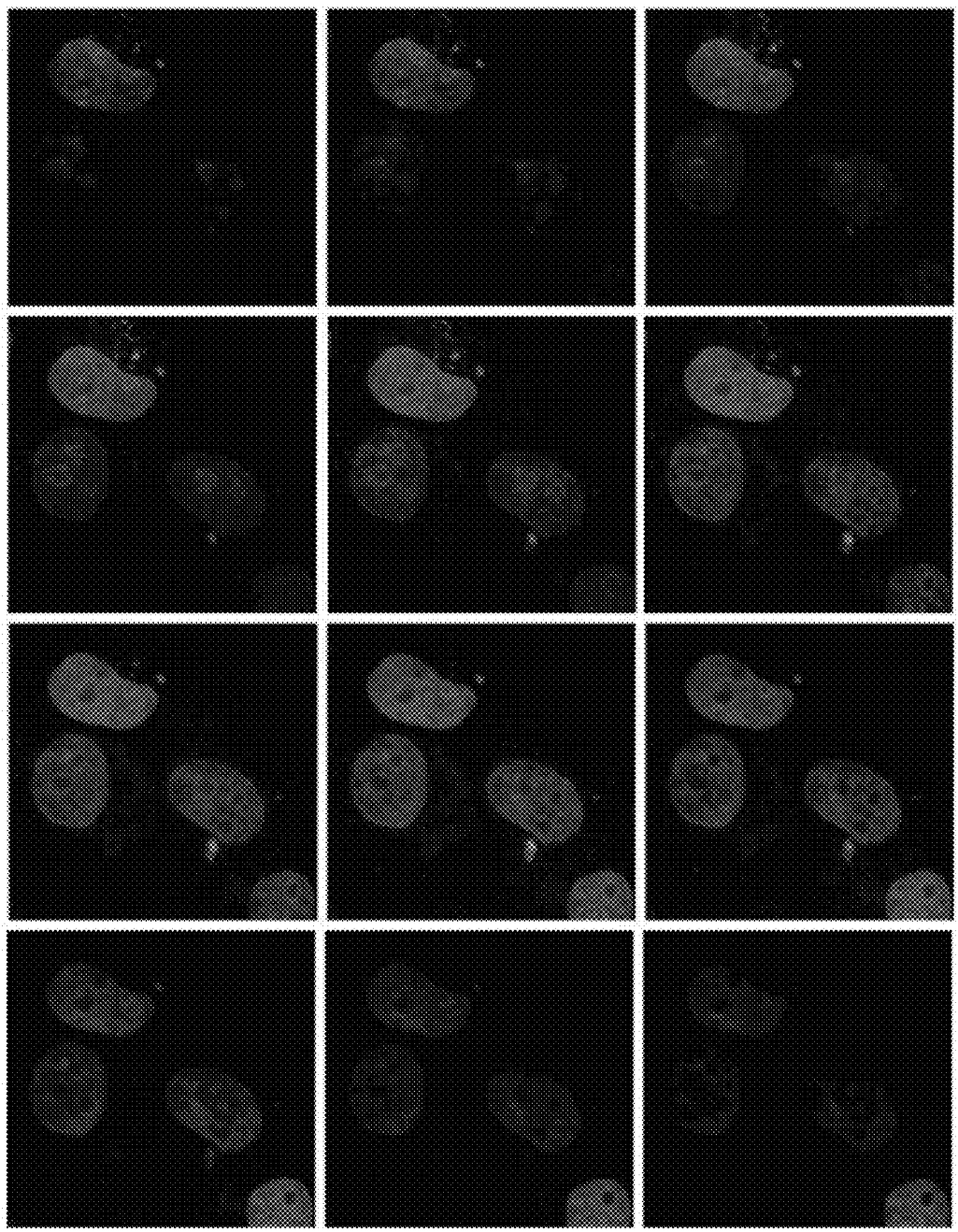

Aptamers RLA01, RLA02, or RLA03 localized on and around membranes of Caov-3 cells, as shown in FIG. 5A. The observed Cy5 fluorescent signals appeared at or near the membranes similarly to that of the Alexa Fluor® WGA stain. All three aptamers localized to the cell membranes (FIG. 5A). In addition, all three localized to multiple compartments within the cytoplasm proximal to the membranes suggesting endosomal internalization. Internalization of Cy5-aptamer (500 nM) conjugates was measured by flow cytometry at 30, 60, 90, and 120 minutes post initial treatment with aptamer RLA01 on Caov-3 cells, as shown in FIG. 5B. Additionally, the percent of internalization events over the same range of time is shown in FIG. 5C. These data were further confirmed by confocal imaging. The endosomal marker pHrodo® Red Transferrin Conjugate was used to identify co-localization of Cy5-aptamer conjugates (5 µM) and endosomal structures. As seen in FIG. 5D pHrodo® Red stained endosomal structures co-localize with Cy5 fluorescent aptamers. These data are highly suggestive that the internalization of aptamers into Caov-3 cells is regulated by endocytic pathways. Moreover, Z-stack imaging (9 stacks, 2 µm range) further demonstrated Cy5 fluorescence within cells consistent with internalization of aptamers (FIG. 6A and FIG. 6B). Thus, confocal imaging of all three Cy5-aptamer conjugates demonstrated fluorescent activity consistent with the average max fluorescent events observed by flow cytometry (FIG. 3A, FIG. 3B, FIG. 3C and FIG. 5).

Confocal Imaging.

Confocal imaging was also employed to further demonstrate aptamer specificity. Cells were seeded at $5.0 \times 10^4$ per well/plate and incubated 37° C. 5% $CO_2$ 48 hours. 2 µL Cy5-aptamer conjugates at concentration ranges of 1 µM to 25 µM was added to 1 mL cell specific media and incubated on target cells 37° C. 5% $CO_2$ 2 hours agitating slightly every 30 minutes on a 35, 0/10 mm glass bottom culture dish and 35, 0/10 mm glass bottom 24 well plate (Greiner bio-one). Cells were washed with PBS (3x) and fixed with 2 ml heptane (1:8.25 PBS: 37% Formaldehyde (Sigma Aldrich)) 37° C. 10 minutes. For endosomal internalization specific microscopy, cells were treated with pHrodo® Red Transferrin Conjugates by the manufacturers' recommended protocol 30 minutes before fixing. Endosomal internalization was observed at 30, 60, 90, and 120 minutes time points post initial treatment with Cy5-aptamer conjugates. Cells were washed with PBS (3x) and fixed with 2 ml heptane (1:8.25 PBS: 37% Formaldehyde (Sigma Aldrich)) 37° C. 10 minutes. Subsequent staining of fixed cells was performed with DAPI (10 ng/µL, 10 minutes), or cell membrane stain Wheat Germ Agglutinin Alexa 488 conjugate (1 µg/µL, 10 minutes, Invitrogen) using standard procedures. Imaging of the cells was done with an Olympus FluoView 1000 confocal microscope using DAPI, Alexa448, pHrodo® Red, and Cy5 filters.

Figure 7A:
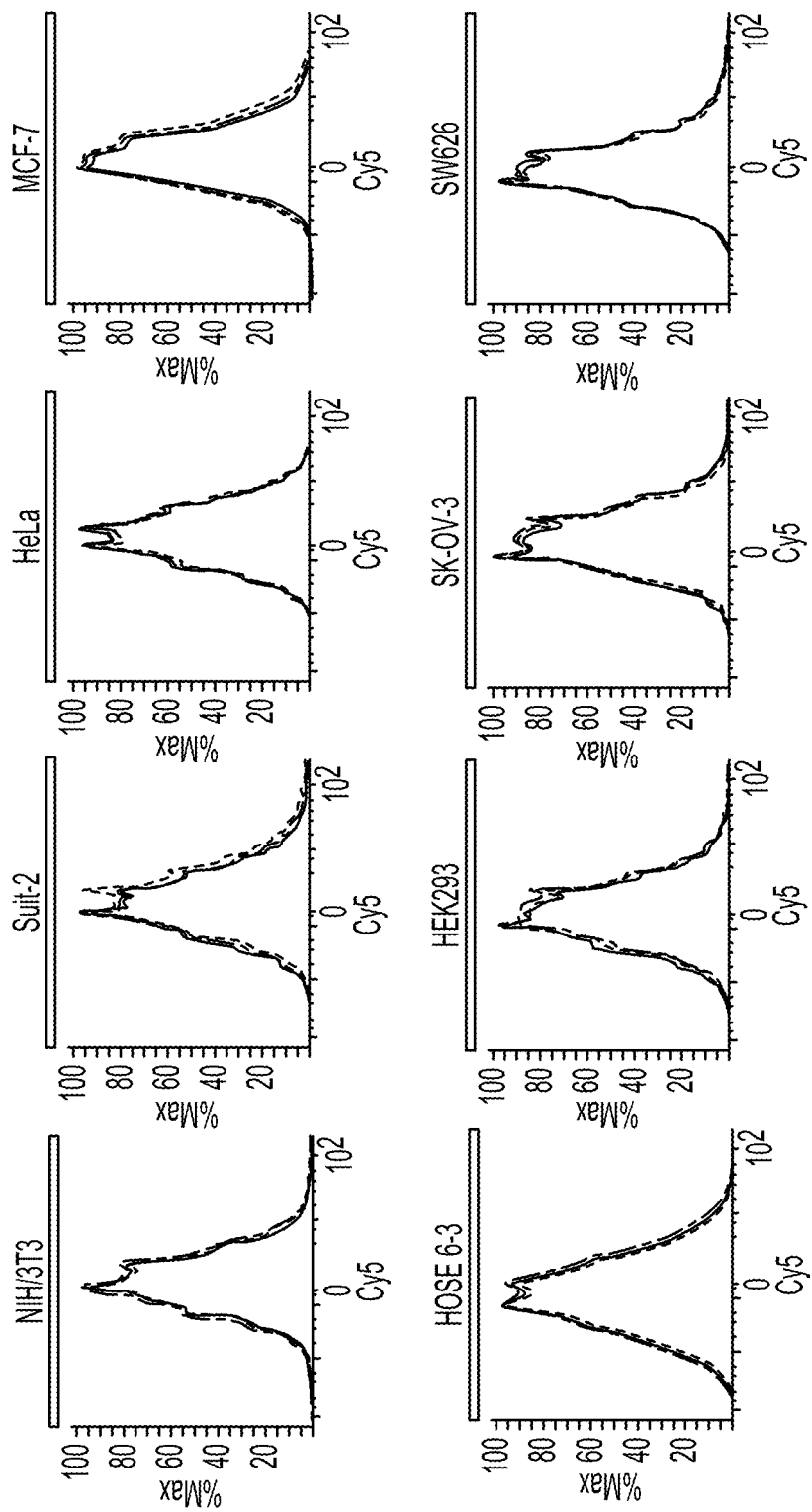
FIG. 7A shows flow cytometry histograms of Cy5-RLA03 conjugates incubated with the following cell lines for 2 hours: epithelial malignancies from breast (MCF-7), pancreatic (Suit-2), cervical (HeLa), and EOC model cell lines SK-OV-3 as well as SW626 were incubated with Cy5-RLA03 aptamer conjugates. Non-malignant immortalized HOSE 6-3 (ovarian epithelial), HEK293 (kidney epithelial), and murine fibroblast (NIH/3T3) were included to demonstrate RLA03 specificity. Cy5-RLA03 doses corresponding to colored hisotgrams are control (solid line), 400 nM ( --- - --- line), and 800 nM ( - - - line) concentrations.
Figure 7B:
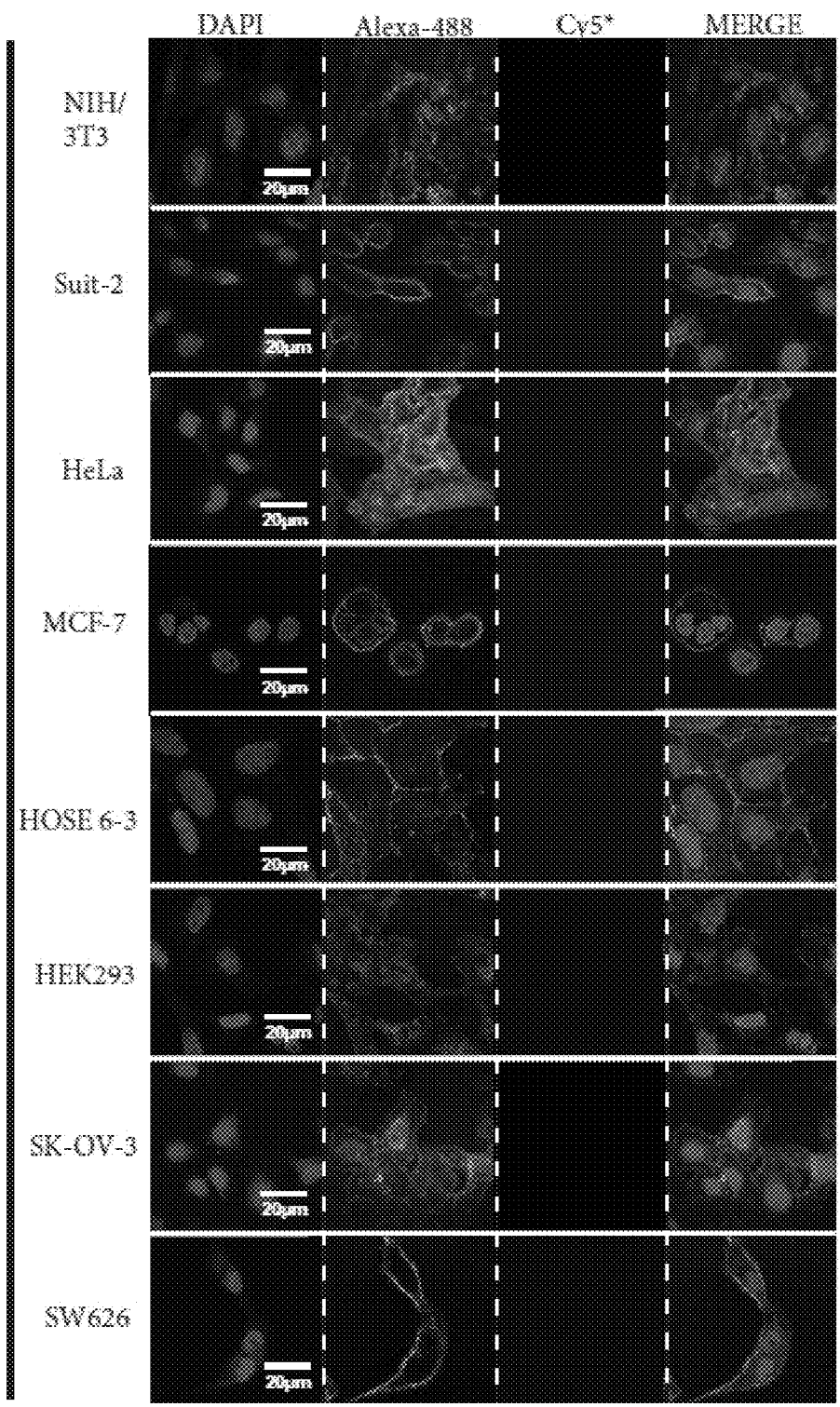
FIG. 7B show confocal microscope images of cells treated with Cy5 conjugated aptamers and incubated at 37° C. for 2 hours. Cells were imaged at 60× using a nuclear stain (DAPI), a membrane stain (WGA-0 . . . Alexa Fluor 488-), and Cy5-aptamers (Cy5 pseudo).

RLA01, RLA02, and RLA03 Caov-3 target aptamers were incubated with a panel of selected EOCs, malignant epithelial, and non-malignant immortalized cell lines, as shown in FIG. 7. Consistent with the flow cytometry histograms shown in FIG. 4A Cy5-RLA01, fluorescent events were not detected above baseline untreated control levels when increasing molar concentrations of Cy5-RLA03 were administered to non-malignant HOSE 6-3 and HEK293 epithelial cell lines (FIG. 7A). Additionally, incubation of Cy5-RLA03 conjugates with malignant epithelial cell lines produced minimal fluorescent events similar to those of untreated control samples. Overall, the full range of Cy5-RLA03 concentrations used for incubation with malignant epithelial cells showed no fluorescent events after a 2 hour incubation period, and this was further supported by confocal imaging (FIG. 7B). Cy5-RLA02 conjugates produced similar data to the Cy5-RLA03 conjugates. Cy5-RLA02 demonstrated no binding to the panel of malignant and non-malignant cell lines. Despite observing detectable fluorescent events when SK-OV-3 and HeLa cell lines were incubated with increasing molar concentrations of RLA01 (FIG. 4D), data obtained by flow cytometry against the panel of malignant and non-malignant cell lines showed no total fluorescent events above untreated control baseline levels, also supported by confocal imaging.

Confocal imaging clearly supports significant internalization of aptamers into specific cell types. Typically it is believed that aptamers internalize into cells via canonical endosomal pathways. The raw confocal images utilizing an endosomal specific marker, as well as Z-stack, generated images support colocalization of Cy5-aptamer signal to internal endosomal membranes.

Example 4: Secondary Structures of the Ovarian Cell Aptamers

Figure 8A:
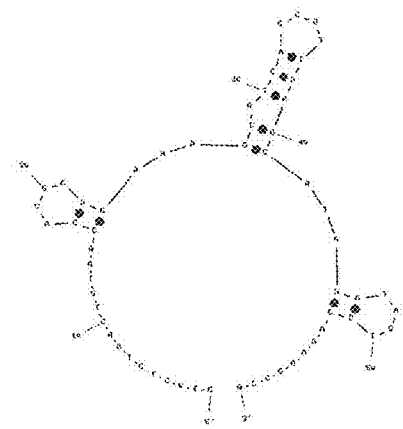
FIG. 8A-8F shows the five top energetically stable predicted secondary structures for RLA01 (SEQ ID NO: 1) as determined by Gibbs free energy (ΔG) using the UNAfold program. The predicted secondary structures yielded the following ΔG values: −2.4 kcal/mol (FIG. 8A); −2.34 kcal/mol (FIG. 8B); −2.24 kcal/mol (FIG. 8C); −2.08 kcal/mol (FIG. 8D); −1.47 kcal/mol (FIG. 8E); −1.43 kcal/mol (FIG. 8F).
Figure 8B:
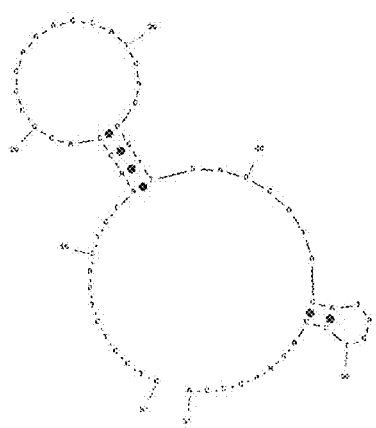
Figure 8C:
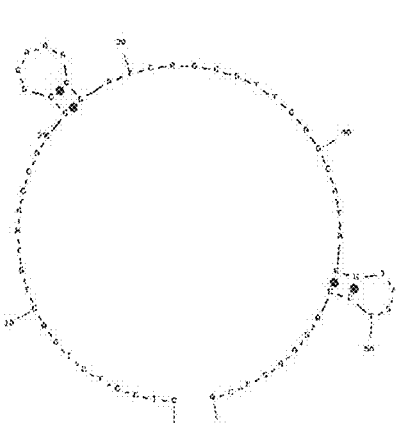
Figure 8D:
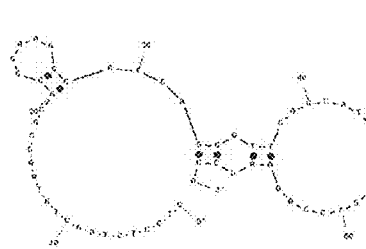
Figure 8E:
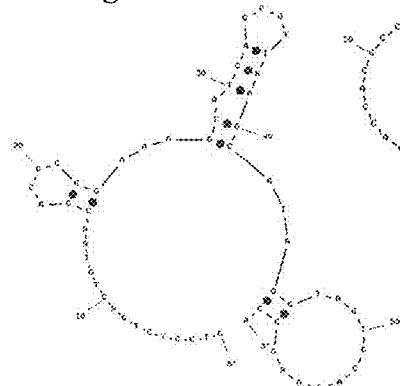
Figure 8F:
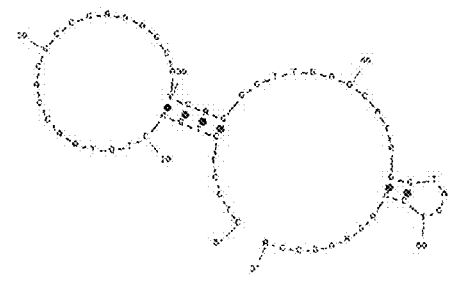
Figure 9A:
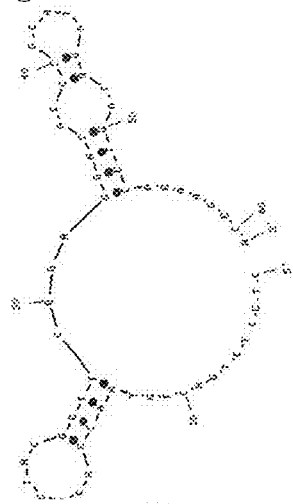
FIG. 9A-9G shows the top six energetically stable predicted secondary structures for RLA02 (SEQ ID NO: 2) as determined by Gibbs free energy (ΔG) using the UNAfold program. The predicted secondary structures yielded the following ΔG values: −4.9 kcal/mol (FIG. 9A); −3.93 kcal/mol (FIG. 9B); −3.72 kcal/mol (FIG. 9C); −3.65 kcal/mol (FIG. 9D); −3 kcal/mol (FIG. 9E); −2.99 kcal/mol (FIG. 9F); −2.8 kcal/mol (FIG. 9G).
Figure 9B:
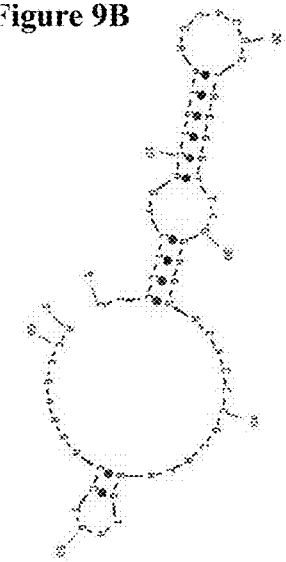
Figure 9C:
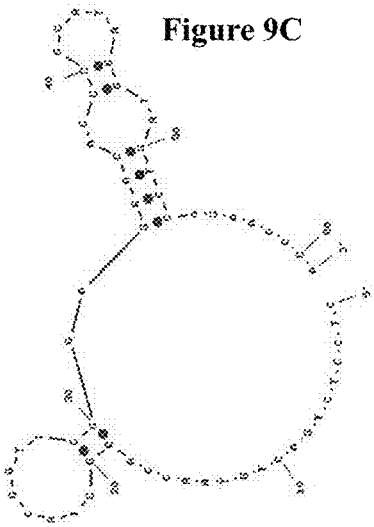
Figure 9D:
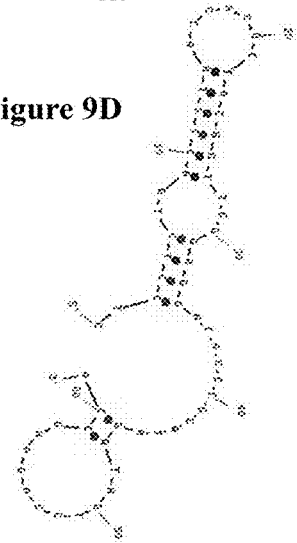
Figure 9E:
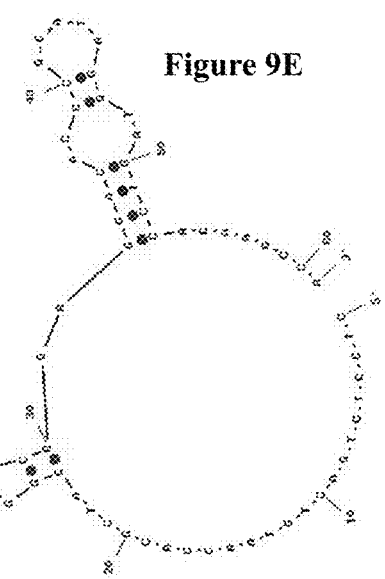
Figure 9F:
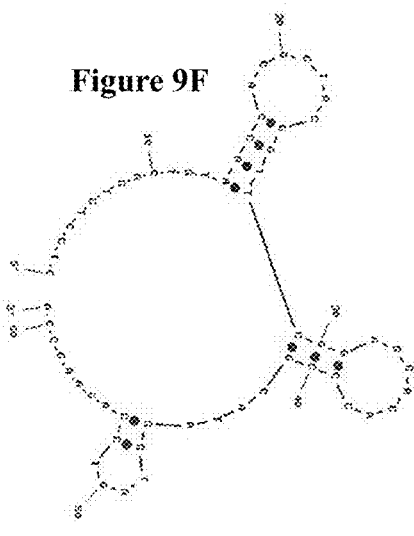
Figure 9G:
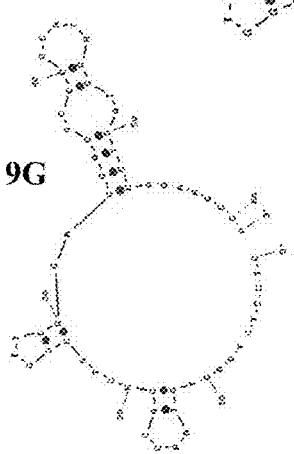
Figure 10A:
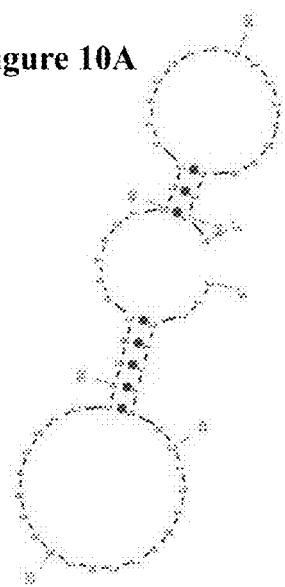
FIG. 10A-10G shows the top six energetically stable predicted secondary structures for RLA03 (SEQ ID NO: 3) as determined by Gibbs free energy (ΔG) using the UNAfold program. The predicted secondary structures yielded the following ΔG values: −4.21 kcal/mol (FIG. 10A); −4.02 kcal/mol (FIG. 10B); −3.39 kcal/mol (FIG. 10C); −2.91 kcal/mol (FIG. 10D); −2.82 kcal/mol (FIG. 10E); −2.22 kcal/mol (FIG. 10F); −2.15 kcal/mol (FIG. 10G).
Figure 10B:
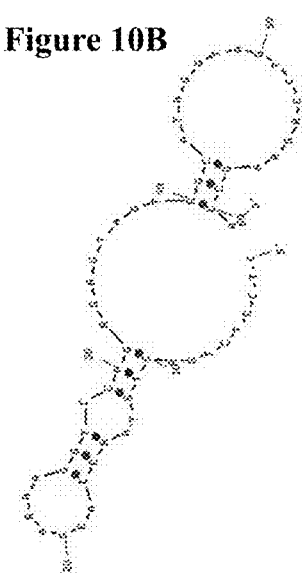
Figure 10C:
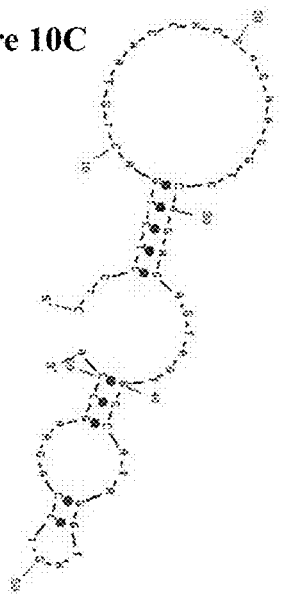
Figure 10D:
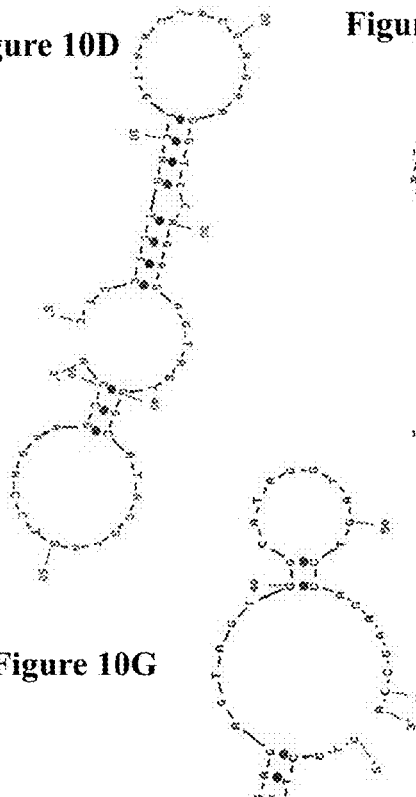
Figure 10E:
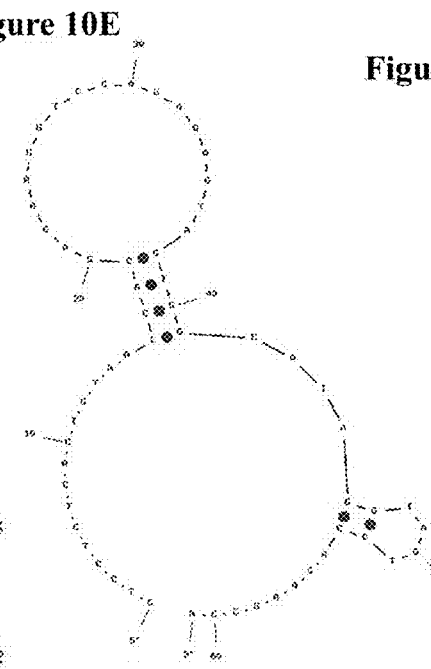
Figure 10F:
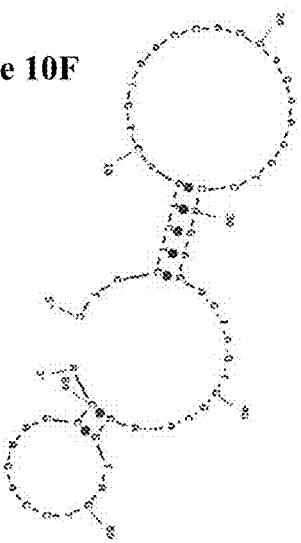
Figure 10G:
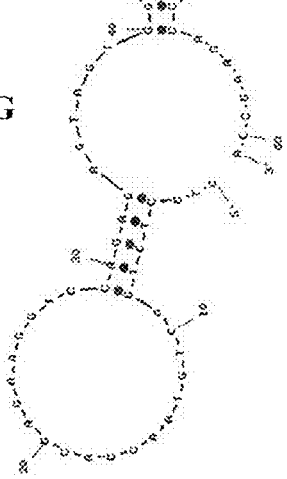
Figure 11A:
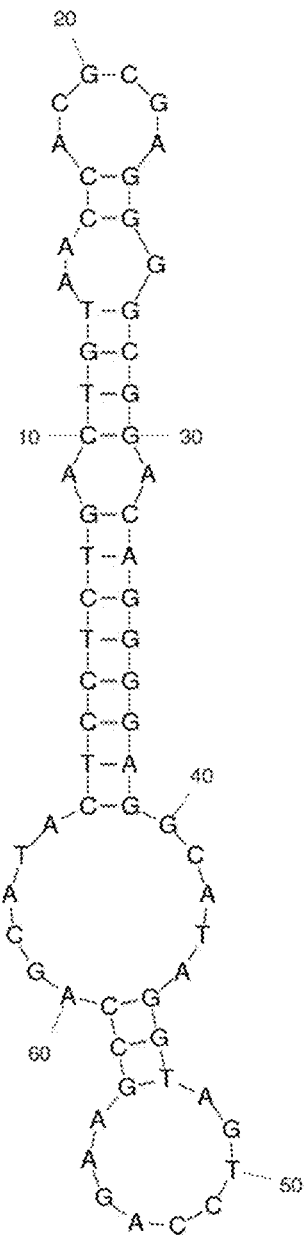
FIG. 11A-11C shows the top three energetically stable predicted secondary structures for RLA04 (SEQ ID NO: 4) as determined by Gibbs free energy (ΔG) using the UNAfold program. The predicted secondary structures yielded the following ΔG values: −1.30 kcal/mol (FIG. 11A); −1.16 kcal/mol (FIG. 11B); −0.89 kcal/mole (FIG. 11C).
Figure 11B:
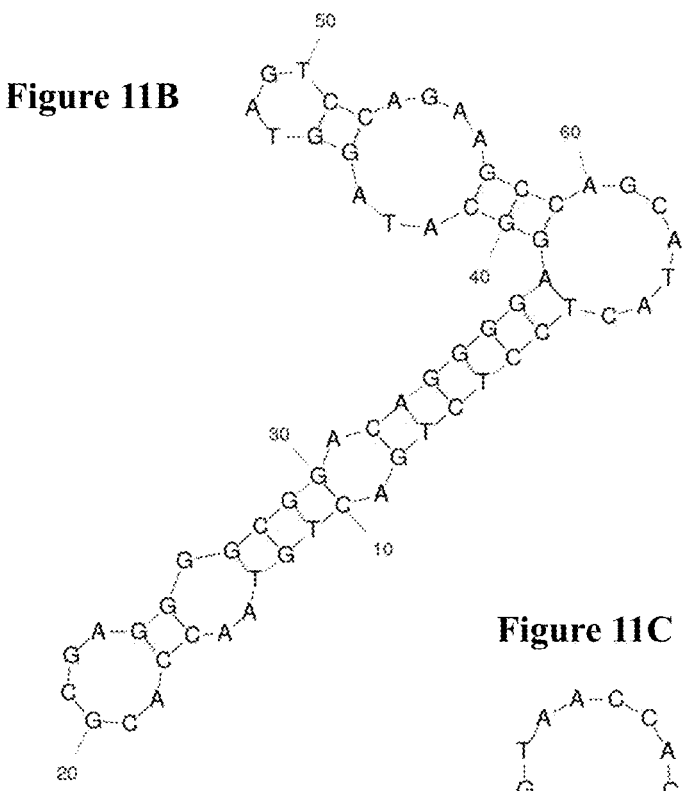
Figure 11C:
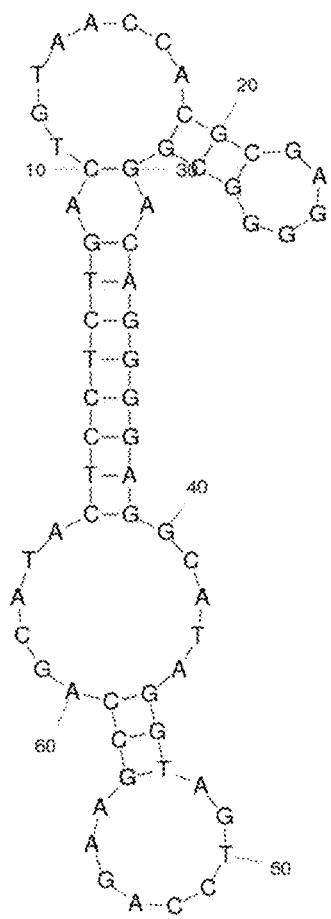
Figure 12:
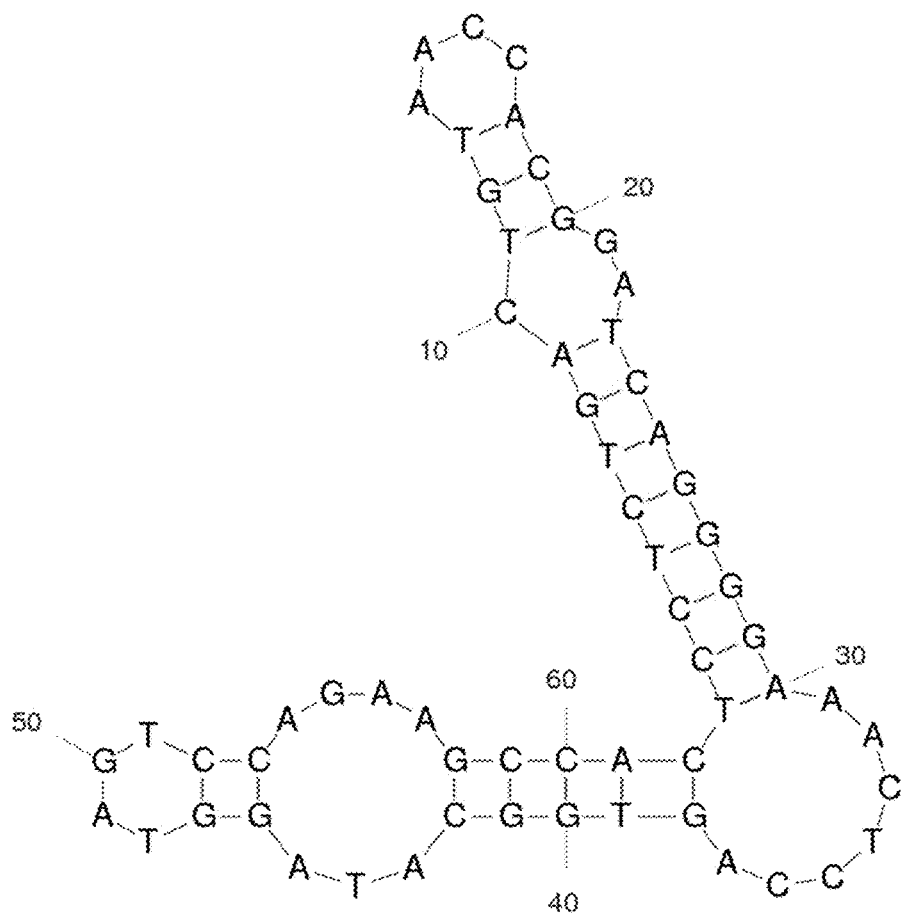
FIG. 12 shows the top energetically stable predicted secondary structure for RLA05 (SEQ ID NO: 5) as determined by Gibbs free energy (ΔG) using the UNAfold program. The predicted secondary structure yielded a ΔG value of −3.68 kcal/mol.
Figure 13A:
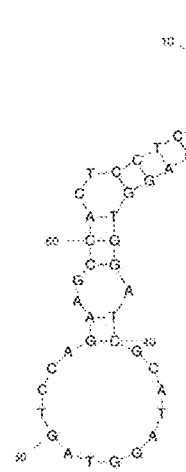
FIG. 13A-13F shows the top six energetically stable predicted secondary structures for RLA06 (SEQ ID NO: 6) as determined by Gibbs free energy (ΔG) using the UNAfold program. The predicted secondary structures yielded the following ΔG values: −2.46 kcal/mol (FIG. 13A); −2.46 kcal/mol (FIG. 13B); −3.01 kcal/mole (FIG. 13C); −3.12 kcal/mol (FIG. 13D); −3.32 kcal/mol (FIG. 13E); −3.4 kcal/mol (FIG. 13F).
Figure 13B:
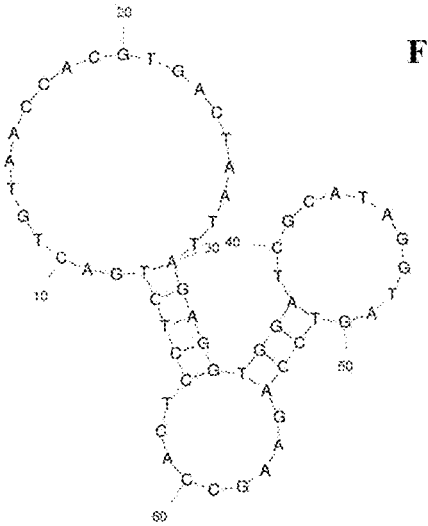
Figure 13C:
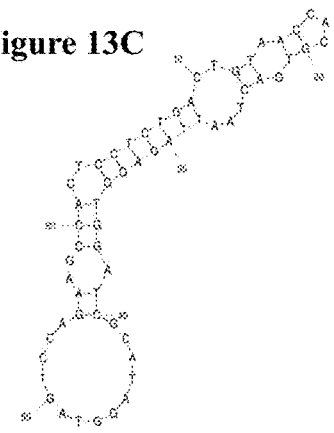
Figure 13D:
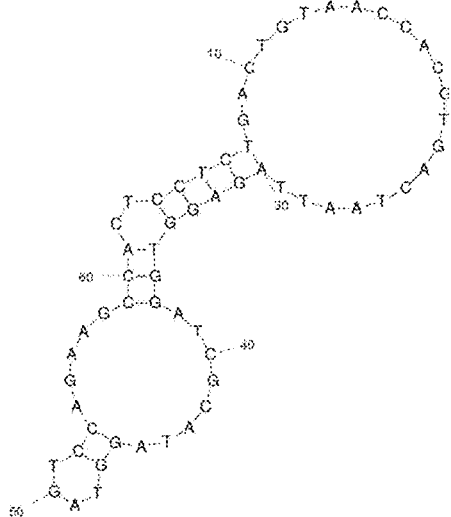
Figure 13E:
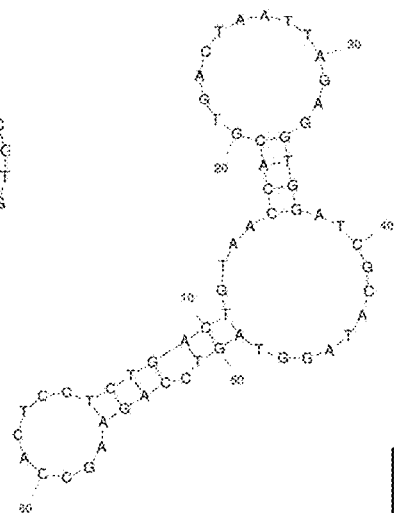
Figure 13F:
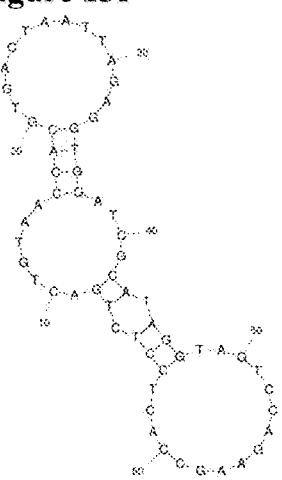
Figure 14A:
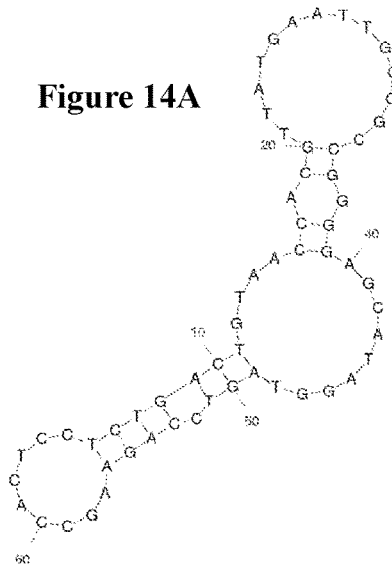
FIG. 14A-14F shows the top six energetically stable predicted secondary structures for RLA07 (SEQ ID NO: 7) as determined by Gibbs free energy (ΔG) using the UNAfold program. The predicted secondary structures yielded the following ΔG values: −3.55 kcal/mol (FIG. 14A); −3.63 kcal/mol (FIG. 14B); −3.74 kcal/mol (FIG. 14C); −3.97 kcal/mol (FIG. 14D); −4.03 kcal/mol (FIG. 14E); −4.21 kcal/mol (FIG. 14F).
Figure 14B:
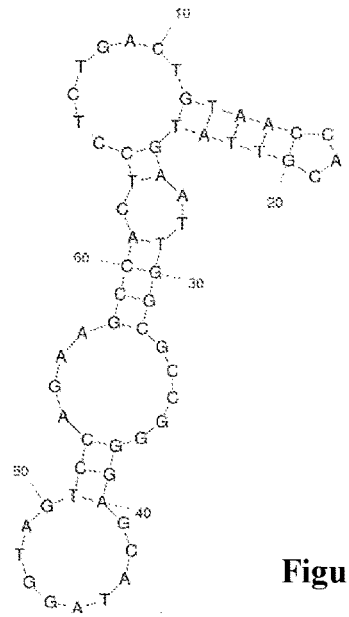
Figure 14C:
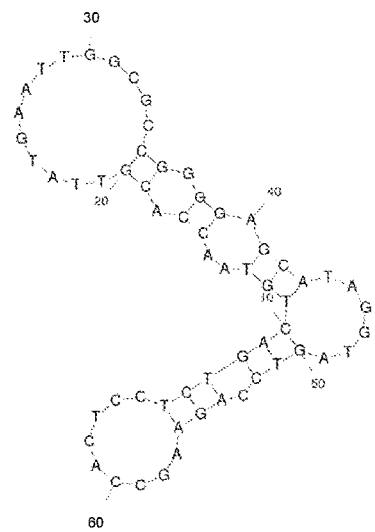
Figure 14D:
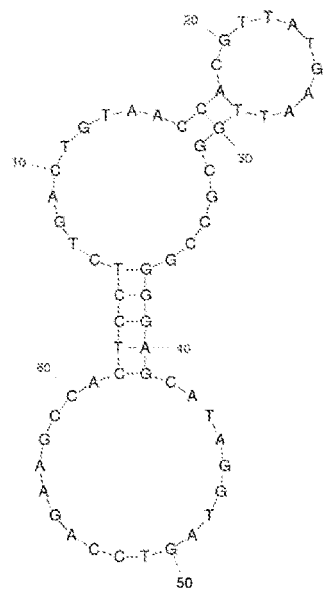
Figure 14E:
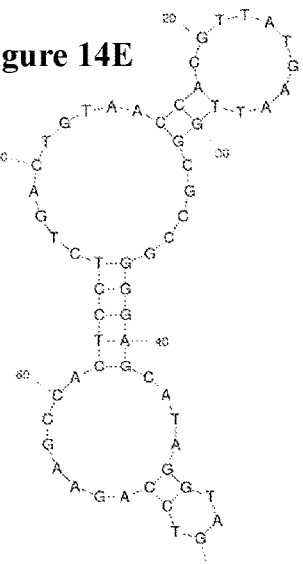
Figure 14F:
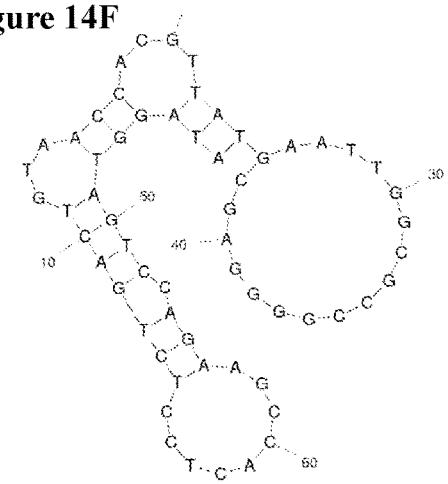

In order to predict the most stable structures for RLA01, RLA02, RLA03, RLA04, RLA05, RLA06, and RLA07, UNAfold (Rensselaer Polytechnic Institute) was used. Ranking of the stability for these aptamers is based on Gibbs free energy ($\Delta G$) analyzed at 20° C. RLA01 yielded a $\Delta G$ value of −2.4 kcal/mol (FIG. 8A). RLA02 yielded a $\Delta G$ value of −4.91 kcal/mol (FIG. 9A). RLA03 yielded a $\Delta G$ value of −4.24 kcal/mol (FIG. 10A). RLA04 yielded a $\Delta G$ value of −1.30 kcal/mole (FIG. 11A). RLA05 yielded a $\Delta G$ value of −3.68 kcal/mole (FIG. 12). RLA06 yielded a $\Delta G$ value of −3.4 kcal/mol (FIG. 13F). RLA07 yielded a $\Delta G$ value of −4.21 kcal/mol (FIG. 14F). RLA01 and RLA02 exhibit a large central loop with small hairpin structures radiating from the main loop, as shown in FIG. 8 and FIG. 9, respectively. RLA03 forms a longer structure consisting of a double hairpin with a central loop, as shown in FIG. 10. Figures detailing the top energetically stable secondary structures of aptamers RLA01, RLA02, RLA03, RLA04, RLA05, RLA06, and RLA07 are shown in FIGS. 8-14.

The aptamers are similar in their 5' and 3' sequences that were used as anchors for PCR amplification during Cell-SELEX. Despite these known identities, the aptamers have different stable predicted structures and hairpin loops that would produce unique surfaces for interactions with target cell membranes. Further support that these aptamers are unique comes from the independent equilibrium binding kinetics of each on Caov-3 cells (described above in Example 2). The confocal imaging was consistent with the total fluorescent events observed by flow cytometry using Cy5 conjugated aptamers with highest levels of internalized aptamer observed with RLA01, followed by RLA03, and lowest with RLA02 (described above in Example 3). Further, RLA01 was determined to bind to a broader spectrum of cell types, as discussed in Example 2. Although others reported identification of ovarian carcinoma specific aptamers, sequence alignment of the RLA01, RLA02, RLA03, RLA04, RLA05, RLA06, and RLA07 shows that they are unique from those previously reported.

Example 5: In Vitro Cell-Specific Aptamer Delivery to Ovarian Tumor Cells for Use in Therapeutic Methods To determine the ability of the aptamers to target and kill EOC cells in vitro, the survival of EOC cells treated with chemotherapy-loaded nanoparticles were conjugated to the RLA01, RLA02, and RLA03 aptamers (SEQ ID NOS: 1-3) was assessed.

Cell proliferation was measured with a Vybrant® MTT Cell Proliferation Assay Kit (Invitrogen, Eugene, Oreg.) according to the manufacturers' protocol. Briefly, polymer nanoparticles were loaded with 0.2 µM paclitaxel, a common chemotherapy drug used to treat ovarian cancer, and conjugated to the aptamers. CAOV-3 cells were seeded into 96-well plates (5000 cells/well) and incubated 24 hours 37° C. 5% $CO_2$. Cells were mixed with indicated treatments for a period of 4 hours 37° C. 5% $CO_2$, washed in 1×PBS (3×), and given fresh media. Cell proliferation was observed at 0, 4, 8, 24, and 48 hours post initial treatment. Cell proliferation activity was evaluated by adding 10 µL MTT stock solution and incubation for 4 hours 37° C. 5% $CO_2$, then addition of 100 µL SDS-HCl solution and allowed to stand for 4-12 hours 37° C. 5% $CO_2$. Resulting solution was pipetted vigorously and the optical density (OD) was measured at 570 nm using a Multiskan GO Microplate Reader (Thermo Scientific, Vantaa, Finland). Time points (shown in FIGS. 15A-15C) mark average OD reading (n=3) at indicated concentrations.

As shown in FIG. 15A (RLA01), FIG. 15B (RLA02), and FIG. 15C (RLA03), PLGA nanoparticles loaded with paclitaxel and coated with aptamer treatments (square) caused a significant decrease in cell proliferation when compared to Paclitaxel alone (circle) and PLGA nanoparticles loaded with paclitaxel (triangle) at the 24 hour and 48 hour time points. PLGA nanoparticles loaded with paclitaxel and coated with aptamer treatments (square) caused a >50% reduction in cell proliferation for all three treatments RLA01, RLA02, RLA03 displayed. Data analyzed by two-way ANOVA significant p-values $p<0.001$.

These results demonstrate that RLA01, RLA02, and RLA03 when conjugated to chemotherapeutic-loaded nanoparticles promote specific tumor cell line killing. These results also demonstrate that chemotherapy-loaded nanoparticles conjugated to the aptamers described herein may be used to deliver a targeted higher local dose of cancer treatment.

To assess the upregulation of pro-apoptotic proteins Caspase-3 and PARP-1, CAOV-3 cells were treated with 0.1 µM concentrations (by weight) of Paclitaxel loaded PLGA nanoparticles coated with RLA01 for 4 hours 37° C. 5% $CO_2$ Untreated cells were also analyzed for baseline protein analysis. Cells were then washed with PBS (3×) and incubated 37° C. 5% $CO_2$. The cells were harvested after 0, 4, 8, 12, 24, and 48 hours post initial treatment. Cell pellets were frozen and stored at −80° C. Protein extraction from cell lysates was collected by Total Protein Extraction Kit (CHEMICON International). Protein concentrations were analyzed by Bio-Rad $D_c$ Protein Assay (Bio-Rad Laboratories, Hercules, Calif.). Equal amount (7 mg) of protein was subjected to electrophoresis on NuPAGE 10% Bis-Tris Gel (Life Technologies) and then transferred to positively charged nylon transfer membrane (GE Healthcare). The blotted membranes were immunostained with primary antibodies specific for Caspase-3 antigens (8G10, Cell Signaling Technology) or PARP1 antigens (H-300, Santa Cruz Biotechnology) then 2° antibody (rabbit-IgG, Santa Cruz Biotechnology). PARP-1 and caspase 3 treated membranes were stripped and immunoblotted with anti-β-actin. The signals were developed by Amershem™ ECL Plus Western Blotting Detection System according to the manufacturer's protocol (GE Healthcare).

As shown in FIG. 15D, a time dependent increase of both PARP-1 and Caspase-3 following treatment with Paclitaxel loaded PLGA nanoparticles coated with RLA01 but not in untreated cells was observed. Upregulated levels of PARP-1 and Caspase-3 appear as early as 8 hours post treatment and are highest at 24 and 48 hour time points consistent with MTT proliferation data.

Example 6: In Vivo Cell-Specific Aptamer Delivery to Ovarian Cancer in a Xenograft Mouse Tumor Model To determine the ability of the aptamers to target EOC cells in vivo, EOC cells were treated with chemotherapy-loaded nanoparticles conjugated to aptamer and localization to EOC cells and cell survival was assessed in mice.

Nu/J (nude) female mice aged 6-8 weeks (obtained from Jackson Labs) were injected in the right rear flank with $1 \times 10^6$ CAOV-3 cells. Mice were monitored until tumor growth and mass were palpable (approximately 100 mm³). Mice were injected via tail vein with 0.1 µM concentrations (by weight) of PLGA nanoparticles loaded with FP650 fluorescent dye and coated with RLA01 aptamer (referred to as "Aptamer" in FIG. 16). Control mice were injected with 0.1 µM concentrations (by weight) of PLGA nanoparticles loaded with FP650 fluorescent dye without RLA01 (referred to as "No Aptamer" in FIG. 16). Total volume was 0.1 mL in 1×PBS. Mice were imaged via IVIS imaging to detect FP650 signal at 0, 4, 8, 24, 48, 72, and 96 hours post-injection. All mice show localization of signal in the tail vein region at the site of infection. Four of five mice injected with nanoparticles coated with RLA01 aptamer show signal in the region of the xenograft tumor beginning at 4 hours and peaking between 8-48 hours then diminishing. By contrast, zero of five mice injected with nanoparticles not coated with aptamer localize to the tumor site.

Figure 16:
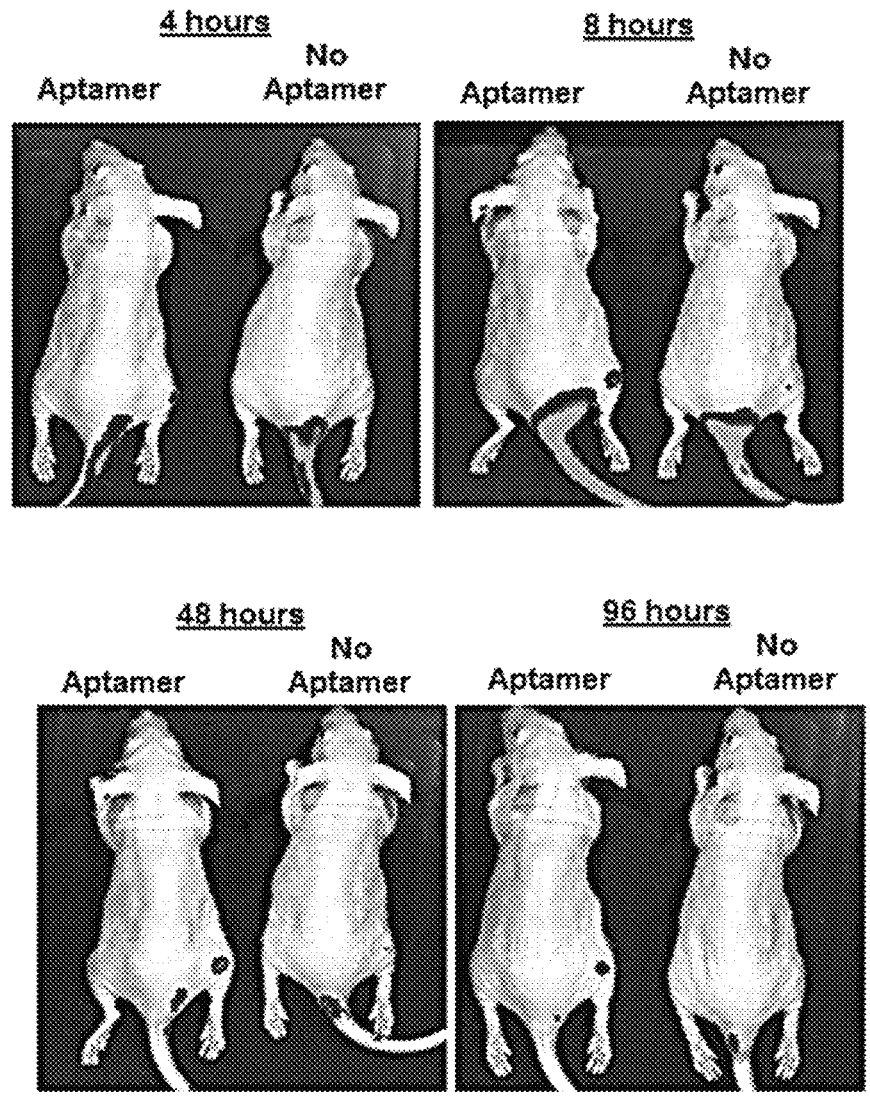
FIG. 16 shows IVIS imaging of mice that were injected via the tail vein with 0.1 μM concentrations (by weight) of PLGA nanoparticles loaded with FP650 fluorescent dye and coated with RLA01 aptamer at 4, 8, 48, and 96 hours post-injection.

In sum, RLA01 (SEQ ID NO: 1), when conjugated to fluorophore-loaded nanoparticles will localize in vivo to the site of an ovarian tumor over 72 hours when injected near the tumor site in a xenograft mouse tumor model. Additionally, RLA01 when conjugated to fluorophore-loaded nanoparticles homed and exclusively localized to the site of an ovarian tumor in vivo over 72 hours when injected via tail vein in a xenograft mouse tumor model (FIG. 16). These results further demonstrate that chemotherapy-loaded nanoparticles conjugated to the aptamers described herein may be used to detect and diagnose ovarian cancer as well as deliver a targeted higher local dose of cancer treatment in a subject.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods described herein are presently representative of preferred embodiments, are exemplary, and are not intended as limitations on the scope of the invention. Changes therein and other uses will occur to those skilled in the art which are encompassed within the spirit of the invention as defined by the scope of the claims.

We claim:

1. An aptamer comprising the nucleotide sequence of CTCCTCTGACTGTAACCACG-$N_x$-GCAT-AGGTAGTCCAGAAGCCA, as set forth in SEQ ID NO: 9, wherein,
   N is a nucleotide selected from the group consisting of G, C, A, and T; and
   x is 19 or 20 nucleotides; and
wherein the aptamer consists of 60 or 61 nucleotides.

2. The aptamer of claim 1, wherein the nucleotide sequence has at least 90% sequence identity to the sequence set forth in SEQ ID NO: 1.

3. The aptamer of claim 1, wherein the nucleotide sequence has the sequence set forth in SEQ ID NO: 1.

4. The aptamer of claim 3, wherein the aptamer binds to a Caov-3 adenocarcinoma cell.

5. The aptamer of claim 3, wherein the aptamer selectively binds to an ovarian tumor cell and not a non-malignant neighboring cell.

6. The aptamer of claim 3, wherein the aptamer is capable of being internalized into an epithelial ovarian cancer (EOC).

7. The aptamer of claim 1, wherein the aptamer is conjugated to a diagnostic agent.

8. The aptamer of claim 7, wherein the diagnostic agent is selected from a radioactive substance, a dye, a contrast agent, a fluorophore molecule, or a bioluminescent molecule.

9. The aptamer of claim 8, wherein the diagnostic agent is a cyanine dye.

10. The aptamer of claim 1, wherein the aptamer is conjugated to a nanoparticle.

11. The aptamer of claim 1, wherein the aptamer is conjugated to a therapeutic agent.

12. The aptamer of claim 11, wherein the therapeutic agent is a chemotherapeutic agent.

13. The aptamer of claim 12, wherein the chemotherapeutic agent is paclitaxel or carboplatin.

14. A pharmaceutical composition comprising the aptamer of claim 1 and a pharmaceutically acceptable carrier.

15. A method of treating ovarian cancer in a subject in need thereof comprising: administering to a subject a therapeutically effective amount of the aptamer of claim 1, wherein the aptamer is conjugated to a therapeutic agent, and wherein the aptamer localizes and binds to an ovarian tumor cell, resulting in internalization of the aptamer.

16. A method of diagnosing ovarian cancer in a subject in need thereof comprising:
   a) contacting an ovarian cell with the aptamer of claim 1, wherein the aptamer is conjugated to a diagnostic agent; and
   b) detecting a signal generated by the diagnostic agent to indicate the presence of an ovarian tumor cell.

17. The aptamer of claim 1, wherein the nucleotide sequence has the sequence set forth in SEQ ID NO: 2.

18. The aptamer of claim 1, wherein the nucleotide sequence has the sequence set forth in SEQ ID NO: 3.

19. The aptamer of claim 1, wherein the nucleotide sequence has the sequence set forth in SEQ ID NO: 4.

20. The aptamer of claim 1, wherein the nucleotide sequence has the sequence set forth in SEQ ID NO: 5.

21. The aptamer of claim 1, wherein the nucleotide sequence has the sequence set forth in SEQ ID NO: 6.

22. The aptamer of claim 1, wherein the nucleotide sequence has the sequence set forth in SEQ ID NO: 7.

* * * * *

SEQUENCE LISTING

<160> NUMBER OF SEQ ID NOS: 11

<210> SEQ ID NO 1
<211> LENGTH: 60
<212> TYPE: DNA
<213> ORGANISM: Artificial Sequence
<220> FEATURE:
<223> OTHER INFORMATION: Synthetic oligonucleotide aptamer

<400> SEQUENCE: 1
ctcctctgac tgtaaccacg cggaaagcat cagggttgag cataggtagt ccagaagcca    60

<210> SEQ ID NO 2
<211> LENGTH: 61
<212> TYPE: DNA
<213> ORGANISM: Artificial Sequence
<220> FEATURE:
<223> OTHER INFORMATION: Synthetic oligonucleotide aptamer

<400> SEQUENCE: 2
ctcctctgac tgtaaccacg agaaggtcca gagagtagtg gcataggtag tccagaagcc    60
a                                                                    61

<210> SEQ ID NO 3
<211> LENGTH: 61
<212> TYPE: DNA
<213> ORGANISM: Artificial Sequence
<220> FEATURE:
<223> OTHER INFORMATION: Synthetic oligonucleotide aptamer

<400> SEQUENCE: 3
ctcctctgac tgtaaccacg ctacggttcg gaggacaccc gcataggtag tccagaagcc    60
a                                                                    61

<210> SEQ ID NO 4
<211> LENGTH: 60
<212> TYPE: DNA
<213> ORGANISM: Artificial Sequence
<220> FEATURE:
<223> OTHER INFORMATION: Synthetic oligonucleotide aptamer

<400> SEQUENCE: 4
ctcctctgac tgtaaccacg cgaggggcgg acaggggagg cataggtagt ccagaagcca    60

<210> SEQ ID NO 5
<211> LENGTH: 61
<212> TYPE: DNA
<213> ORGANISM: Artificial Sequence
<220> FEATURE:
<223> OTHER INFORMATION: Synthetic oligonucleotide aptamer

<400> SEQUENCE: 5
ctcctctgac tgtaaccacg gatcagggga aactccagtg gcataggtag tccagaagcc    60
a                                                                    61

```
<210> SEQ ID NO 6
<211> LENGTH: 61
<212> TYPE: DNA
<213> ORGANISM: Artificial Sequence
<220> FEATURE:
<223> OTHER INFORMATION: Synthetic oligonucleotide aptamer

<400> SEQUENCE: 6
ctcctctgac tgtaaccacg tgactaatta gaggtggatc gcataggtag tccagaagcc     60
a                                                                     61

<210> SEQ ID NO 7
<211> LENGTH: 61
<212> TYPE: DNA
<213> ORGANISM: Artificial Sequence
<220> FEATURE:
<223> OTHER INFORMATION: Synthetic oligonucleotide aptamer

<400> SEQUENCE: 7
ctcctctgac tgtaaccacg ttatgaattg gcgccgggga gcataggtag tccagaagcc     60
a                                                                     61

<210> SEQ ID NO 8
<211> LENGTH: 61
<212> TYPE: DNA
<213> ORGANISM: Artificial Sequence
<220> FEATURE:
<223> OTHER INFORMATION: Synthetic oligonucleotide aptamer

<400> SEQUENCE: 8
actcaacgaa cgctgtggat gcgacatagc tagcagcgca tatgtatgta catggacatc     60
t                                                                     61

<210> SEQ ID NO 9
<211> LENGTH: 61
<212> TYPE: DNA
<213> ORGANISM: Artificial Sequence
<220> FEATURE:
<223> OTHER INFORMATION: Synthetic oligonucleotide aptamer
<220> FEATURE:
<221> NAME/KEY: misc_feature
<222> LOCATION: (21)..(40)
<223> OTHER INFORMATION: n is a, c, g, t, or absent, and this region may
      contain 19 or 20 nucleotides

<400> SEQUENCE: 9
ctcctctgac tgtaaccacg nnnnnnnnnn nnnnnnnnnn gcataggtag tccagaagcc     60
a                                                                     61

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
gaggagactg acattggtgc                                                  20

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide
```

```
<400> SEQUENCE: 11
cgtatccatc aggtcttcgg a                                          21
```